US009459158B2

(12) United States Patent
Yildizyan et al.

(10) Patent No.: US 9,459,158 B2
(45) Date of Patent: Oct. 4, 2016

(54) THERMOMETER WITH AGE SPECIFIC FEATURE SELECTION

(75) Inventors: Aleksan Yildizyan, Waltham, MA (US); Rich Thrush, Jersey City, NJ (US); Kelly White, Hudson, MA (US); Amanda Jane Wilson, Needham, MA (US); Ali Cem Yildirim, Cambridge, MA (US); Richard McDuffie, Worcester, MA (US)

(73) Assignee: Helen of Troy Limited, St. Michael (BB)

( * ) Notice: Subject to any disclaimer, the term of this patent is extended or adjusted under 35 U.S.C. 154(b) by 51 days.

(21) Appl. No.: 12/966,697

(22) Filed: Dec. 13, 2010

(65) Prior Publication Data

US 2012/0150482 A1 Jun. 14, 2012

(51) Int. Cl.
| | |
|---|---|
| *G01K 3/00* | (2006.01) |
| *G01K 7/00* | (2006.01) |
| *G01K 13/00* | (2006.01) |
| *A61B 5/01* | (2006.01) |
| *G01K 1/02* | (2006.01) |

(52) U.S. Cl.
CPC ............... *G01K 13/002* (2013.01); *A61B 5/01* (2013.01); *G01K 1/02* (2013.01)

(58) Field of Classification Search
USPC ........................................ 374/163, 107, 169
See application file for complete search history.

(56) References Cited

U.S. PATENT DOCUMENTS

| | | | |
|---|---|---|---|
| 3,494,196 A | 2/1970 | Moussette | |
| 4,536,851 A * | 8/1985 | Germanton | G01K 1/028 374/102 |
| 4,541,734 A * | 9/1985 | Ishizaka | G01K 7/42 374/169 |

(Continued)

FOREIGN PATENT DOCUMENTS

| | | | |
|---|---|---|---|
| JP | 62242828 A | * | 10/1987 |
| JP | A-H3-74023 | | 3/1991 |

(Continued)

OTHER PUBLICATIONS

International Preliminary Report on Patentability for PCT/US/2011/064470, mailed on Oct. 31, 2013.

*Primary Examiner* — Mirellys Jagan
(74) *Attorney, Agent, or Firm* — Stroock & Stroock & Lavan LLP

(57) ABSTRACT

The invention includes a thermometer with a backlight and a method for lighting the backlight. The thermometer has temperature sensing tip, a processor taking temperature readings and determining a sensed temperature reading of the living being from the temperature sensing tip. The thermometer also includes a display and a backlight for lighting the display. The backlight is activated upon a command from the processor and the processor determines whether to activate the backlight based upon the temperature readings. The method embodiment can includes the steps of using the processor to monitor a temperature change indicated by a temperature sensing element. The processor then detects a temperature decrease and activates a first color light emitting element to backlight a display if the temperature decrease exceeds or equals a predetermined threshold. The thermometer is operable in one of a plurality of selectable operating modes, and the predetermined threshold is dependent upon the selected operating mode. For example, operating modes may depend on patient age range or measurement location. Age range may include infant, toddler and adult.

58 Claims, 13 Drawing Sheets

(56) References Cited

U.S. PATENT DOCUMENTS

| | | | |
|---|---|---|---|
| 4,718,775 A * | 1/1988 | Keznickl | 374/104 |
| 5,108,265 A | 4/1992 | Koike | |
| 5,725,087 A | 3/1998 | Ives | |
| 5,738,441 A * | 4/1998 | Cambridge | G01K 7/42 374/102 |
| 5,829,878 A * | 11/1998 | Weiss et al. | 374/163 |
| 6,036,617 A | 3/2000 | Kidokoro et al. | |
| 6,939,039 B2 | 9/2005 | Brunvoll | |
| 7,314,310 B2 | 1/2008 | Medero | |
| 7,549,792 B2 | 6/2009 | Bisch et al. | |
| 7,785,266 B2 | 8/2010 | Fraden | |
| 2002/0082798 A1 | 6/2002 | Kanevsky et al. | |
| 2005/0283261 A1 | 12/2005 | Leung | |
| 2006/0291535 A1 | 12/2006 | Craig et al. | |
| 2007/0076778 A1 | 4/2007 | Frick et al. | |
| 2008/0112464 A1 | 5/2008 | Yerlikaya et al. | |
| 2008/0151965 A1 * | 6/2008 | Kim | 374/162 |
| 2009/0175317 A1 | 7/2009 | Chan et al. | |
| 2009/0178908 A1 | 7/2009 | Ishino et al. | |
| 2010/0250909 A1 | 9/2010 | Waldhoff et al. | |
| 2011/0194585 A1 * | 8/2011 | Shrivastava | 374/120 |

FOREIGN PATENT DOCUMENTS

| | | |
|---|---|---|
| JP | A-H11-141670 | 5/1999 |
| JP | 2004-507729 | 3/2004 |
| JP | A-2007-514137 | 5/2007 |
| JP | A-2008-502903 | 1/2008 |
| JP | A-2008-544287 | 12/2008 |
| JP | A-2009-165618 | 7/2009 |

* cited by examiner

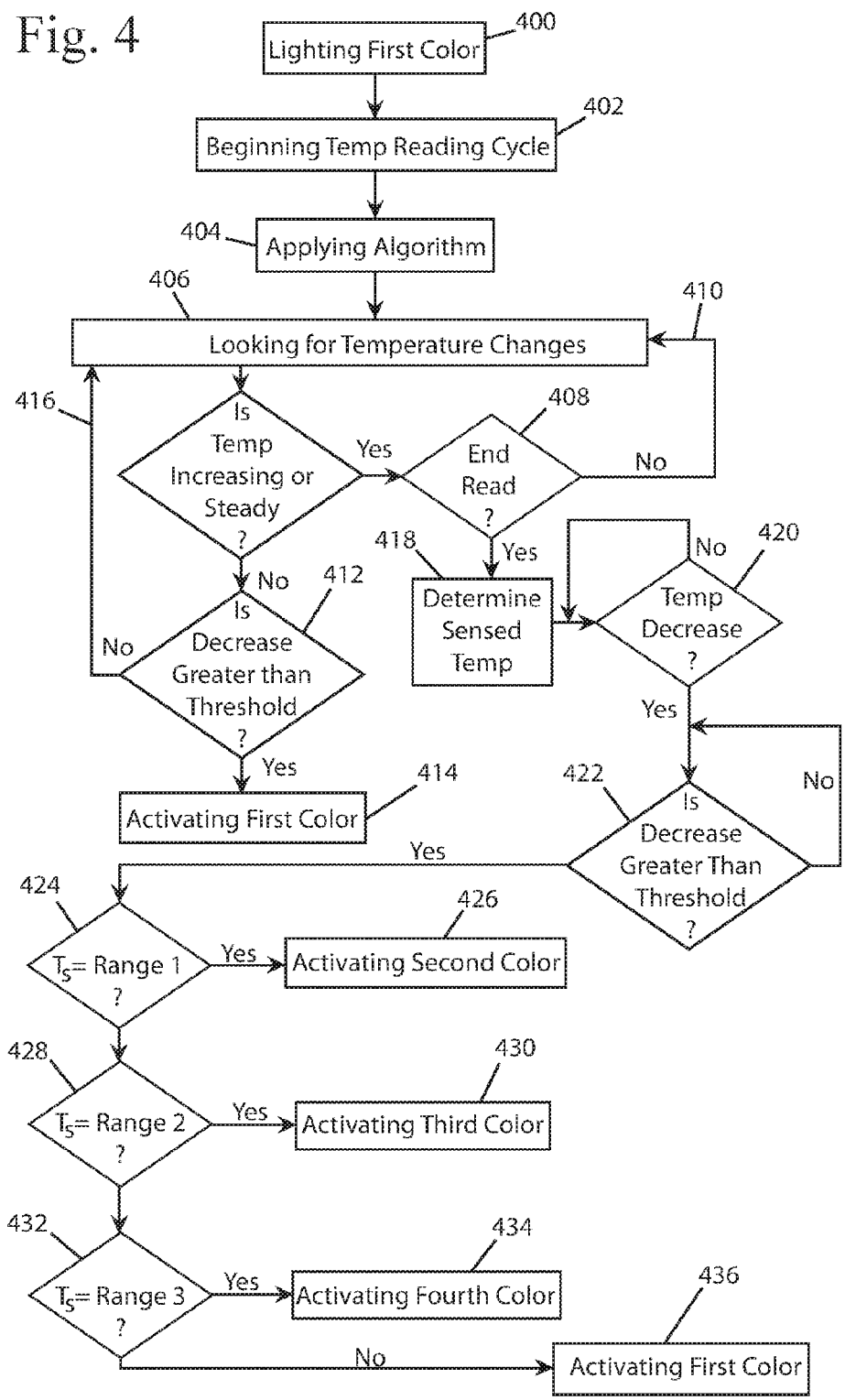

THERMOMETER WITH AGE SPECIFIC FEATURE SELECTION

FIELD OF THE INVENTION

The present invention relates to an electronic thermometer for detecting and visually displaying ranges of body temperature of a patient. More particularly, the present invention pertains to a clinical thermometer with one or more visual indicators that are personalized to a trait of the patient.

BACKGROUND OF INVENTION

There are multiple types of thermometers, including hand held electronic thermometers and glass-tube mercury thermometers. The glass-tube mercury thermometers have gradated scales colored or etched into the glass tube and once the mercury rises and settles in the glass tube due to the temperature of the patient, a user can read the temperature from the scale, calibrated for Fahrenheit or Centigrade. Glass-tube thermometers have a number of drawbacks, including the difficulty of reading a temperature from the gradated scale based on the mercury level.

As an improvement, hand held electronic thermometers have been introduced. In the basic electronic thermometer design, a temperature sensing element is connected to a combined, battery-powered computing and display element. The display element is typically a viewing window provided for the temperature display wherein the temperature is displayed numerically in either Fahrenheit or Centigrade. The multi-segment liquid crystal display (LCD) displays of the electronic thermometers are simple to read and can provide a patient's temperature in tenths of a degree.

However, regardless of the means to display the patient's temperature, the user still must remember the proper temperature ranges for normal, warm and fever conditions. Furthermore, these ranges may vary depending upon one or more traits of the patient, such as age, or upon a measurement location, such as oral, rectal, underarm, forehead, behind the ear, etc. For example, it is known that the temperature range associated with a normal body temperature, a low fever, and a high fever can vary with the age of the patient. Newborns (e.g., about 0-3 months) have a range of normal body temperature of 97.3° F. to 100.3° F., and have fever (including high fever) at ≥100.4° F. Because infancy is a critical age for fever, any fever at a temperature ≥100.4° F. is considered severe. On the other hand, toddlers (e.g., about 3-36 months) have a range of normal body temperature of 96.6° F. to 100.5° F., a low fever range of ≥100.6° F. to 102.2° F., and a high fever range of >102.2° F. Older persons (e.g., age greater than 36 months to adulthood) have a range of normal body temperature of 95.7° F. to 99.9° F., a low fever range of ≥100.0° F.-103.0° F., and a high fever range of ≥102.2° F. Typically a user must consult a guide or chart to determine if the temperature read poses a threat to the patient.

Additionally, while an electronic thermometer is easier to read than a glass-tube thermometer, it can still be difficult to read for those with poor vision. Thus, conventional thermometers lack a cost-effective, easily identifiable indication of the measured temperature.

U.S. Pat. No. 7,350,973 to Craig et al. ("Craig") discloses a color changing thermometer with a backlight and a method for lighting the backlight. The thermometer has a temperature sensing tip and a processor that takes temperature readings and determines a sensed temperature reading of a living being from the temperature sensing tip. The thermometer also includes a display and a backlight for lighting the display. The backlight is activated upon a command from the processor and the processor determines whether a decrease in the temperature readings exceeds or is equal to a predetermined threshold in order to activate the backlight. The method embodiment can includes the steps of using the processor to monitor a temperature change indicated by a temperature sensing element. The processor then detects a temperature decrease and activates a first color light emitting element to backlight a display if the temperature decrease exceeds or equals a predetermined threshold.

U.S. Pat. No. 5,829,878 to Weiss et al. ("Weiss") discloses a thermometer that lights a backlight only on the detection that the temperature reading is complete. If the temperature reading is not completed, the backlight will not be activated. Thus, if the patient accidentally interrupts the reading, the patient will not receive the benefit of the backlight to enable them to see the display. Also, in one embodiment, Weiss' thermometer shuts the backlight off after a predetermined time. If the patient leaves the thermometer in place after the reading longer than the predetermined time, the patient will not get the benefit of the backlight when the patient actually reads the displayed temperature.

In an alternate embodiment, Weiss discloses that the backlight does not shut off until the on/off switch is pressed. This can lead to a drain on the battery and lower the service life of both the battery and the thermometer. The thermometer can be left in the patient for a significant amount of time, if the caregiver is away from the patient attending to other matters. Weiss' thermometer will be backlit the entire time, draining the battery unnecessarily.

A number of U.S. patents disclose thermometers with audible alarms if a patient's temperature is high enough to indicate a fever or once the reading is completed. For example, U.S. Pat. No. 5,165,798 to Watanabe describes an electronic thermometer with an electronic buzzer that is used to indicate the completion of a temperature measurement. Watanabe does not disclose an indicator based on the specific temperature of the particular patient.

U.S. Pat. No. 5,923,258 to Tseng discloses an electronic thermometer designed to display a digital temperature signal under all temperature reading conditions. Tseng then produces a fever alarm indication by optionally flashing the temperature readout and/or sounding a buzzer. Thus, if the patient does not have a fever, the user must still read the display to determine the temperature of the patient. Tseng does not provide audio or visual signals for any other temperature range.

Visual signals identifying the relative temperature of an engine's cooling water are also known. U.S. Pat. No. 6,778,095 to Lo discloses pointer-type meters for vehicles and linking a gradated color scale to the reading determined by the meter. As an initial point, Lo does not relate to thermometry for living beings. Further, Lo does not sense the temperature of the water directly, but senses the displacement of the pointer needle and lights the appropriately colored light. Lo must sense the physical displacement of the pointer to allow the system to be interchangeable with any pointer-type meter. Thus, Lo requires a pointer-type meter and triggers the illumination indirectly by reading the physical displacement of the pointer and not the actual temperature.

U.S. Pat. No. 6,441,726 to Voto et al. ("Voto") also discloses a warning system for a vehicle instrument cluster wherein the gages can be backlit or have a gradated color scale. The colored lights can be steady on/off or can flash. As with Lo, Voto does not relate to thermometry for living beings. Additionally, Voto does not replace the standard display, but illuminates the standard gauges in a vehicle instrument cluster. Thus, the user may be confronted with a confusing display of both analogue and colored visual stimuli.

Further, using either Lo's or Voto's inventions in a thermometer for living beings is both size and cost prohibitive, since both a readout display and a colored scale display must be included. When included in the cost of a vehicle, the additional cost for the visual system is nominal. However, for a thermometer designed for living beings, it can be a substantial proportion of the cost to include both displays.

Thus, there is a need in the art for a low cost, easy to read, colored visual display for a thermometer meant for living beings.

Further, there is a need in the art for a low cost, easy to read, colored visual display for a thermometer meant for living beings that activates the backlight once the thermometer is removed from the patient.

SUMMARY OF THE INVENTION

In one embodiment, an electronic thermometer has a temperature sensing element connected to a powered processor, a mode selection switch and a display. The components are housed in a case having a probe section and a body section. A typical case can be a rigid plastic or any other material.

The processor, mode selection switch and display are secured in the body section of the case and the body section can include a power/initialization button. The temperature sensing element is mounted at the end of the probe section and is covered with a conductive cap.

The processor can receive signals from the temperature sensing element related to the temperature of the living being, i.e., the patient, and can convert the signals to a temperature in either Fahrenheit or Centigrade. The temperature sensing element may operate by various sensing methods, such as by directly contacting the patient, or by sensing infrared ("IR") emissions from the patient. The temperature may be sensed in various body locations on or in the patient, such as mouth, rectum, behind the ear, ear canal, underarm, forehead, etc. Certain body locations are more suitably measured using some sensing methods, but not by other sensing methods. The processor can also include a memory for storing at least one set of ranges of temperatures and an adjustment for the display. The processor can compare the currently read temperature to the stored temperature ranges and adjustment values to determine which element of the display to illuminate.

A plurality of sets of temperature ranges can be stored in memory, each set of temperature ranges corresponding to a different measurement mode. A discrete number of measurement modes may be provided, each measurement mode corresponding to a different measurement condition such as a characteristic of the patient or a measurement location on or in the patient. The mode selection switch provides a mechanism to select from among the available measurement modes and associated sets of temperature ranges. An output indicator provides feedback to the user (i.e., either the patient or an attendant) of what measurement mode has been selected.

The display can include a transparent or "see-through" liquid crystal display (LCD) to display the actual temperature. The body section is formed with an opening, hole, or recess and the LCD is placed inside. The user can see through the LCD and thus through the case. One or more lighting elements, which in an embodiment, can be light emitting diodes (LEDs) or similar light emitting elements, are disposed in the display and peripheral to the LCD. The light emitting element can backlight the display to illuminate the LCD or be the sole temperature display.

In one embodiment, the light emitting element is capable of generating different colored light to backlight the display. For example, the light emitting element can generate a first, second, third, and fourth color.

In another embodiment, the display can include a translucent liquid crystal display (LCD). The LCD can be any shape, including rectangular and octagonal and can be a "reverse" LCD. A reverse LCD lights the numerals of the display instead of the background. This increases the visibility and viewing angle of the LCD.

The display can further include a transparent lens. In an embodiment, the lens can be circular, elliptical, or any other shape to form the display. One or more lighting elements are disposed in the display and peripheral to the LCD. The light emitting element edge lights the display to illuminate the LCD.

The light emitting element is capable of generating different colored light to edge light the display. For example, the light emitting element can generate a first, second, and third color. The first color, which in an embodiment is green, can correspond to a range of temperatures indicating a "normal" temperature of the patient. The second color can be yellow and can indicate that the patient has a low fever and is "warmer" than normal. The third color, which can be red, can indicate that the patient has a high fever. Additionally, more than one light emitting element can correspond to the chosen temperature range or multiple light emitting elements can be illuminated at one time. For instance, more light emitting elements may be lit in order to draw attention to a high fever.

The display includes multiple lighting elements, which can be light emitting diodes (LEDs) or similar light emitting elements. A first light emitting element can be a first color. A second light emitting element can be a second color, a third light emitting element can be a third color and a fourth light emitting element can be a fourth color, etc.

In an embodiment, the first color can be white and illuminated once the power/initialization button is pressed and can indicate that the thermometer is ready to read a temperature. The second light emitting element can illuminate the second color, green, which can indicate a "normal" temperature of the patient for the selected measurement mode. The third color emitted by the third light emitting element can be yellow to indicate that the patient has a low fever and is "warmer" than normal for the selected measurement mode. The fourth light emitting element has the fourth color of red that indicates a high fever when the temperature of the patient is greater than a predetermined threshold for the selected measurement mode.

In use, in an embodiment the user presses the power/initialization button and waits for the first light emitting element to light indicating that thermometer is ready to read a temperature. The user selects a measurement mode, thereby setting the limits of the temperature ranges. This embodiment may be suitable for either electronically or mechanically actuated mode select switches. In another embodiment, the measurement mode may be selected first, and then the user presses the power/initialization button. This latter embodiment may be more suitable for mechanically actuated mode select switches.

The user then places the probe section in contact with the patient to sense the temperature thereof. As the processor receives the temperature signal, it accesses memory to determine which range the read temperature falls into. The processor then intermittently lights the second light emitting element as the temperature is being read. The flashing second light emitting element indicates that the reading is not complete. Once the reading is complete, the second light emitting element can be illuminated steadily, indicating to the user that the reading is complete and that the temperature of the patent falls within the "green" range.

If the temperature of the patient increases during the reading, the third and fourth light emitting elements can also be intermittently lit. The third light emitting element can flash and steadily illuminate the third color while the reading is within the range calibrated for the third color. Further, if the temperature of the patient dictates, the fourth light emitting element can flash and then turn steady to indicate that the reading is complete and the patient has a fever. Thus, as the reading is being taken, the light emitting elements transition from the first to the fourth color while flashing and then steadily illuminate the light emitting element corresponding to the actual temperature of the patient. Additionally, more than one light emitting element can correspond to the chosen temperature range or multiple light emitting elements can be illuminated at one time.

A method to activate the backlight emitting element has the steps of the thermometer beginning the temperature reading cycle and the processor taking the readings from the temperature sensing element. The processor can look for a temperature increase and if a temperature increase is detected, it applies an algorithm to determine the temperature of the patient, such as a "peak and hold" and a "predictive" algorithm, to the readings. If the processor detects a temperature decrease, it determines if the decrease is greater than or equal to a preprogrammed threshold. If the temperature drop is greater than or equal to the preprogrammed threshold, the processor activates the backlight emitting element. The reason for activating the light emitting element when a temperature drop equals or exceeds the predetermined threshold, is that this is an indicator that the thermometer has been removed from the patient. When the thermometer is removed from the patient, the thermometer typically undergoes a temperature drop since it is going from the relatively warm body environment to the relatively cooler air outside the body. If the temperature drop is not greater than or equal to the threshold, the processor continues to take readings to determine if the temperature is increasing or decreasing.

Alternatively, once the algorithm is complete, the processor looks for a decrease in temperature and if the temperature drop is greater than or equal to a preprogrammed threshold, the processor activates the backlight emitting element. If the temperature drop is not greater than the threshold, the processor continues to take readings to determine if the temperature is decreasing.

The preprogrammed threshold can be based on temperature, time, or number of readings. The temperature threshold can be if the temperature drops between about 0.1 to about 5° (either Fahrenheit or Centigrade). In one embodiment, the threshold temperature amount is about 0.1°. Alternately, the threshold can be deter mined based on the amount of time it takes to achieve a significant drop in temperature without having the patient wait too long for the backlight to activate. This time can vary between about 1 to about 6 seconds. The rate of change in temperature can vary based on the difference in temperature compared to that of the ambient air. Further, evaporation may cause the temperature to drop faster when removed from the mouth, compared to removal from a drier location such as the underarm or behind the ear.

Further, the threshold can be the number of readings in which the temperature drops. The number of readings can vary between 1 and about 10,000, depending on the sampling rate of the thermometer and the length of time the thermometer is sampling. Thus, if the processor reads one or more temperatures where the current reading decreases from the previous reading, the backlight is triggered.

In another embodiment, the backlight may be activated prior to the detection of a sufficient temperature drop. For instance, the backlight may be activated when the temperature readings plateau, or when the rate of increase of the temperature readings drops below a predetermined positive rate. This may correspond to a time when the temperature measurement is substantially completed, and/or a time when the thermometer has been removed, prior to the occurrence of a sufficient drop in temperature.

Another method includes a thermometer lighting the first color to indicate that the thermometer is ready to read a temperature from the temperature sensing element. In one embodiment, the first color can remain illuminated throughout the entire read cycle or shut off after a specific amount of time or once the temperature reading is begun.

The temperature reading cycle begins and the processor can take the readings from the temperature sensing element. The processor applies an algorithm and looks for a temperature change. If the temperature is increasing or steady, the processor determines if the temperature reading has ended and may continue to apply the algorithm. If the processor detects a temperature decrease, it determines if the decrease is greater than or equal to a preprogrammed threshold. If the temperature drop is greater than or equal to the preprogrammed threshold, the processor activates the first color. If the temperature drop is not greater than or equal to the threshold, the processor continues to take readings to determine if the temperature is increasing or decreasing.

Once the algorithm has ended, the processor determines the sensed temperature and then looks for a decrease in temperature. If the temperature drop is greater than or equal to the preprogrammed threshold, the processor compares the sensed temperature to a first range and if the sensed temperature falls within the first range, the second color is illuminated. If the sensed temperature does not fall within the first range, the processor determines if it falls within a second range, and if so, illuminates the third color. If the sensed temperature does not fall within the second range, the processor determines if it falls within a third range, and if so, illuminates the fourth color. If the sensed temperature does not fall within the three ranges, the first color can be illuminated.

For example, when a patient activates the thermometer, a white light emitting element can be activated. The processor starts a temperature read and can optionally turn off the white light emitting element. If the patient removes the thermometer in the middle of the temperature read, the processor detects the decrease in temperature and activates the white light emitting element. If the patient leaves the thermometer in place until the temperature reading is complete, the processor then waits to detect a temperature decrease. Once the patient removes the thermometer from the temperature sensing position, the temperature of the temperature sensing element drops and is detected by the processor. The processor detects the drop and determines if the drop is larger than a preprogrammed threshold. If the drop is large enough, the processor determines if the sensed temperature falls within the above-discussed predetermined ranges. The processor then illuminates either the green, yellow, or red light emitting element depending on which range the sensed temperature falls into.

Embodiments include a thermometer for use with a living being having a temperature sensing tip, a processor taking temperature readings and determining a sensed temperature reading of the living being from the temperature sensing tip. The thermometer also includes a display and a backlight for lighting the display. The backlight is activated upon a command from the processor and the processor determines whether a decrease in the temperature readings exceeds a predetermined temperature amount in order to activate the backlight.

A method embodiment includes the steps of using a processor to monitor a temperature change indicated by a temperature sensing element. The processor then detects a temperature decrease and activates a first color light emitting element to backlight a display if the temperature decrease exceeds a predetermined amount.

Embodiments can include changing the color scheme to be any range of colors. Alternately, all of the light emitting elements can be one element capable of emitting a range of colors. The light emitting elements can be differing shades of the same base color. For example, the second color can be a darker green than first color. The same shading scheme can be used for third and fourth light emitting elements.

Further, multiple light emitting elements can be illuminated to form the necessary colors. An embodiment can utilize a color scale of blue, green and yellow, where blue and yellow light emitting elements illuminate to form the green color in the display. Further, intensities of certain base colors can be used to form any and every color. For example, combinations of red, blue and green can form many colors of the spectrum and these base colors can be used solely to be combined to form the first through fourth colors of the above embodiments. The base colors themselves may not be a color in the selected range.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 4 is a flow diagram illustrating a method of illuminating multiple colored backlights of the present invention;

DETAILED DESCRIPTION

Figure 1:
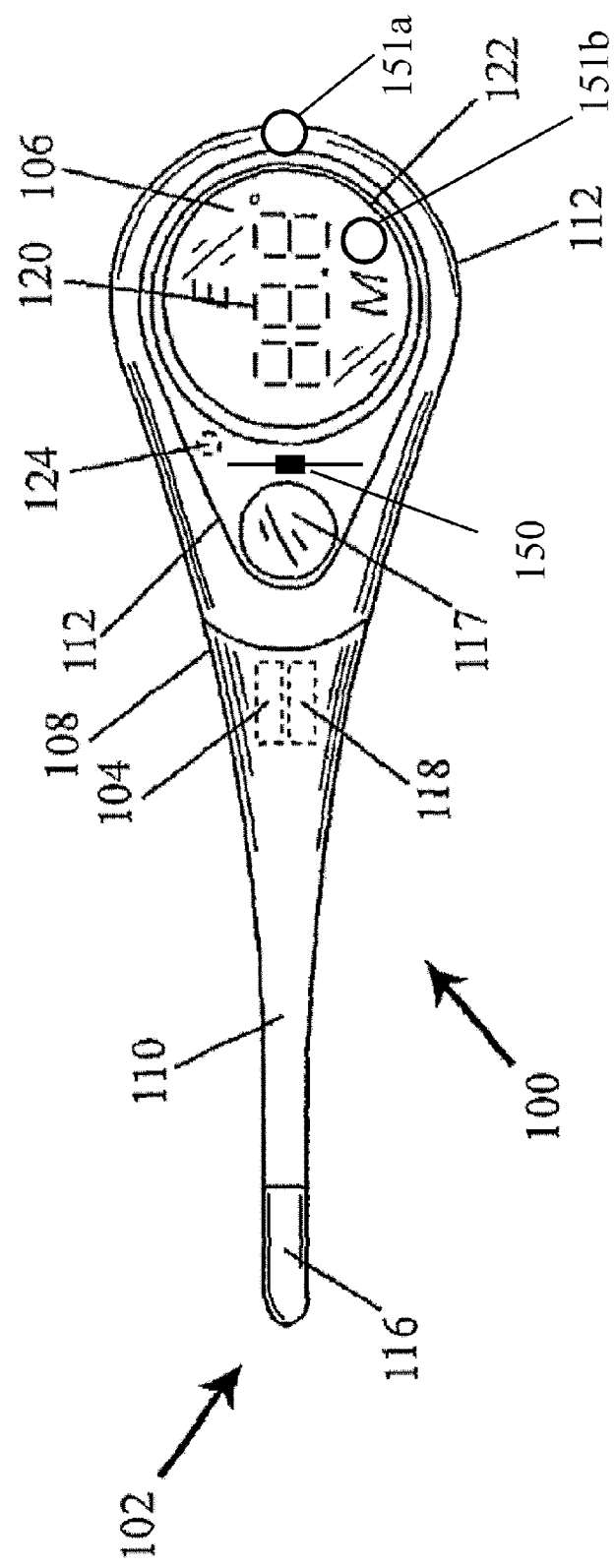
FIG. 1 is a top view of a color display thermometer of the present invention.

Referring to FIG. 1, an embodiment of an electronic thermometer 100 for use with a living being is illustrated. A temperature sensing element 102 is connected to a powered processor 104 and/or a display 106. The components are housed in a case 108 having a probe section 110 and a body section 112.

The processor 104 and display 106, and in one embodiment a battery (not illustrated), are secured in the body section 112 of rigid case 108 along with an access door (not illustrated), optionally provided for battery replacement. Further, body section 112 can include a power/initialization button 117. The temperature sensing element 102 is mounted at the end of probe section 110 and covered with a conductive cap 116. The conductive cap 116 can be, for example, metal.

The processor 104 can receive signals from temperature sensing element 102 related to the temperature of the living being, i.e., the patient. The processor 104 can convert the signals to a temperature in either Fahrenheit or Centigrade. The processor 104 can also include a memory 118 for storing ranges of temperatures and an adjustment for the display 106. Processor 104 can compare the currently read temperature to the stored temperatures and adjustment values to determine what color to illuminate the display 106.

The processor 104 may have more than one measurement mode, in which at least some of the measurement modes are tailored to at least a first trait of a patient, or tailored for different usage of the electronic thermometer 100. For instance, patient age may be a first trait, and so there may be separate measurement modes for newborns (e.g., less than about 3 months old), toddlers (e.g., about 3 to about 36 months old), and adult (e.g., about 36 months and older). The number of measurement modes may be greater or less than three. The measurement modes may also be based on a second patient trait (e.g., body mass index), either separately or in combination with the first trait. The measurement mode may also depend on usage of the electronic thermometer 100, e.g., oral, rectal, and underarm temperature measurements. Operation of processor 104 may change in response to the mode selection by, for example, changing the temperature ranges associated with high, normal, and low temperature readings.

Temperature ranges for newborns, toddlers, and adult that are associated with a normal body temperature, a low fever, and a high fever are known in the art. At a first level of granularity this provides three measurement modes. The ranges can be further refined to take into account known variations due to measurement locations such as oral, rectal, and underarm, providing additional measurement modes. The ranges can be programmed into the electronic thermometer 100 at the time of manufacture, or can be updated later by way of a firmware or software change.

Embodiments of the invention are not limited by the technology employed by the temperature sensing element 102. The temperature sensing element 102 may operate by direct contact with a body part to be sensed, or may operate without direct contact such as by detection of infrared ("IR") emanations from the body part to be sensed. IR-operated temperature sensing elements 102 may be useful for some body part locations such as the ear canal or forehead, but not practical for other body part locations such as in the mouth or rectum. Direct contact operated temperature sensing elements 102 may be useful for body part locations such as underarm or in the mouth or rectum, but not preferable for other locations, such as in the ear canal where direct contact may risk a punctured eardrum.

The display 106 can include a transparent or "see-through" liquid crystal display (LCD) 120 for displaying the actual temperature, and in an embodiment, to a tenth of a degree. The body section 112 is formed with an opening or recess 122 and the LCD 120 is placed inside. The user can see through LCD 120 and thus through case 108. One or more lighting elements 124, which in an embodiment, can be light emitting diodes (LEDs) or similar light emitting elements, are disposed in the display 106 and peripheral to LCD 120. The backlight emitting element 124 backlights the display 106 to illuminate the LCD 120. LEDs 124 can also be the used without the display 106 and be used as the sole display of a sensed temperature Ts.

The electronic thermometer 100 includes a mode select switch 150. The mode select switch 150 can be used to select among the available measurement modes of the processor 104. The embodiment of FIG. 1 illustrates mode select switch 150 as a slide switch, which can be useful for selecting from among a discrete number of modes corresponding to discrete positions or detents of mode select switch 150. A slide switch could also be configured to interpolate temperature limits based on a position of the switch between discrete switch positions that correspond to the discrete number of modes. A slide switch embodiment can include all types of slide switches, such as electronic, mechanical and electro-mechanical. A mode selection switch 150 that is actuated at least partially by mechanical methods may be settable to a desired mode when the electronic thermometer 100 is either on or off.

Figure 13:
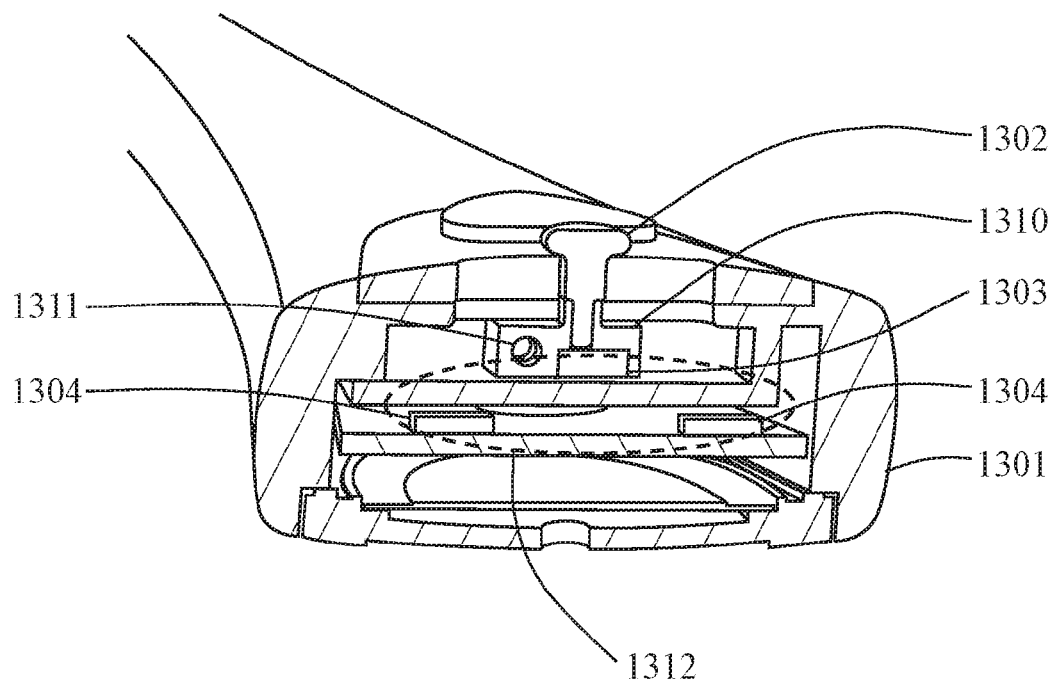
FIG. 13 is a cutaway view of a first embodiment of a mode select switch.

FIG. 13 illustrates a cutaway view of a slide switch embodiment of the mode select switch 150. A Hall Effect sensor 1312 is formed from the combination of magnet 1303 and one or more Hall elements 1304. The Hall Effect sensor 1312 is used to sense the position of the slide switch within thermometer housing 1301. A user operates the slide switch by moving knob 1302 left or right. Knob 1302 is attached to body 1310. Body 1310 holds magnet 1303 such that magnet 1303 moves along with knob 1302. As magnet 1303 moves left and right, it approaches one of two Hall elements 1304 and recedes from the other of the two Hall elements 1304, thereby generating an electrical positioning signal by way of the Hall Effect. Persons of skill in the art will recognize that a Hall effect sensor 1312 may be operable with a different number of Hall elements 1304, such as one Hall element 1304. Thermometer housing 1301 has mechanically affixed one or more spring-loaded engagement balls (not shown in FIG. 13). The spring end of spring-loaded engagement balls is affixed to the thermometer housing 1301 and the ball end of the spring-loaded engagement ball engages with indentation 1311 on body 1310, thereby providing a stop location for knob 1302. Knob 1302 can be disengaged from the spring-loaded engagement ball by the application of a moderate amount of sliding force. Alternatively, the spring-loaded engagement ball can be affixed to body 1310 and one or more engaging indentations 1311 can be located on thermometer housing 1301.

Figure 14:
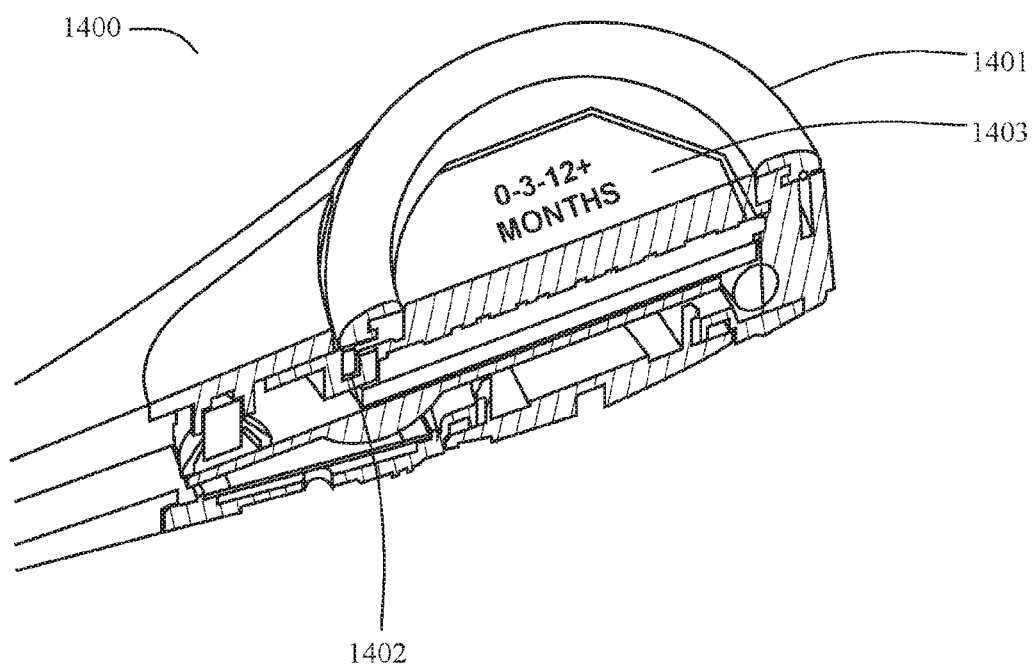
FIG. 14 is a cutaway view of a second embodiment of a mode select switch.

Another embodiment of a mode select switch may be a rotary switch. FIG. 14 illustrates a cutaway view of a rotary switch embodiment 1400 of the mode select switch 150, implemented as a rotary ring around the display 1403, rotating in a plane parallel to the plane of display 1403 and having an axis of rotation perpendicular to the display 1403, such that turning the rotary switch (clockwise and/or counterclockwise) can select and/or switch between age groups. The rotary switch may also be implemented as a thumbwheel embedded into a surface (either major or edge surface), such that the axis of rotation of the rotary switch is parallel to the plane of the surface. The rotary switch can include any type of physical designs, such as electronic, mechanical and electro-mechanical.

Referring again to FIG. 14, the user controls the rotary switch 1400 by rotating the bezel 1401, which forms the rotary ring around the display 1403. One or more Hall elements 1402 magnetically engage with one or more magnets (not shown in FIG. 14) that are physically coupled to bezel 1401 and which move as bezel 1401 is rotated. Detents may provide discrete and repeatable stopping locations for bezel 1401.

Figure 15:
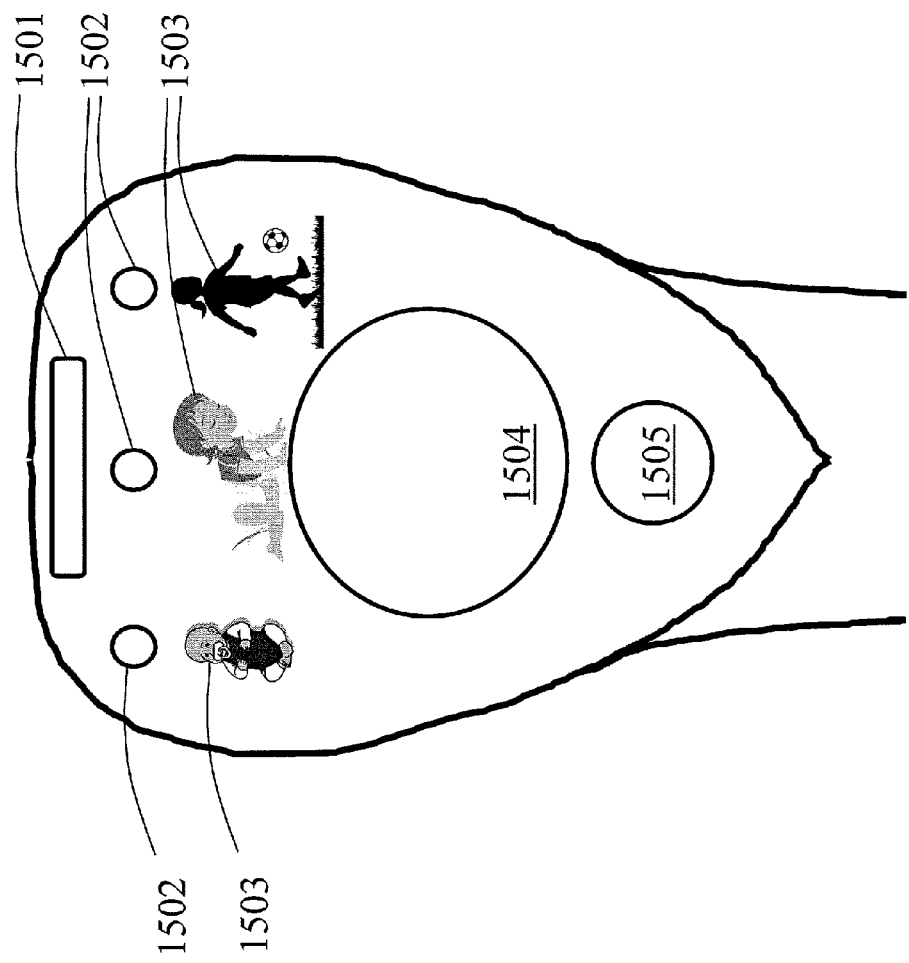
FIG. 15 is a plan view of a third embodiment of a mode select switch.

Referring now to FIG. 15, another embodiment of a mode select switch may include a secondary button 1501 wherein successive presses of the secondary button will cycle the processor 104 among the available modes. One or more indicators 1502 can be provided to indicate the currently-selected mode. Indicators 1502 may be, for example, a separate light for each mode, or a single light having a changeable characteristic such as color or intensity, or a transient indicator such as a different number of blinks or an audible indicator when the mode is changed. A visual indicator such as text or a graphic 1503 may accompany one or more of indicators 1502 as a reminder to the user of the respective measurement mode. The embodiment includes output display 1504 and power/initialization button 1505. A secondary button embodiment can include any type of button switches, such as electronic, mechanical and electro-mechanical.

Figure 16:
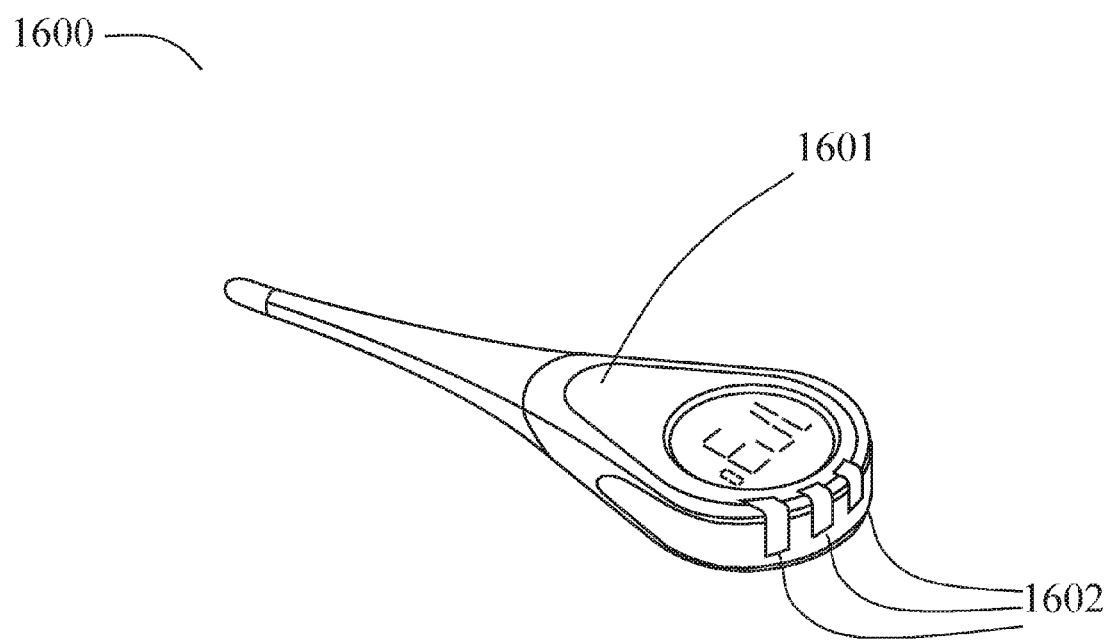
FIG. 16 is a perspective view of a fourth embodiment of a mode select switch.

Referring now to FIG. 16, another embodiment of a mode select switch may incorporate the mode select switching function into other controls of electronic thermometer 1600. For instance, short taps of power/initialization button 1601 can be used to select among the available measurement modes, while holding down power/initialization button 1601 can be used to turn on/off the electronic thermometer 1600. As with the embodiment of FIG. 15, one or more indicators 1602 can be provided to indicate the currently-selected more. Indicators 1602 may be, for example, a separate light for each mode, or a single light having a changeable characteristic such as color or intensity, or a transient indicator such as a different number of blinks or an audible indicator when the mode is changed. The embodiment of FIG. 16 illustrates indicators 1602 as three tri-color LEDs (i.e., LEDs controllably capable of emitting one of three different colors), which are each illuminated once the thermometer has finished taking the measurement. In the illustrated embodiment, each of indicators 1602 corresponds to a respective measurement mode, with the color (green, yellow, or red) of each LED indicating normal, low fever, or high fever for the respective measurement mode.

Another embodiment of mode select switch 150 may include usage of a touchscreen, a touchscreen being an electronic visual display that can detect the pressure and location of a touch within the display area. Touching the touchscreen of electronic thermometer 100 with a finger or hand can be used to select and/or switch between the available measurement modes.

Another embodiment of mode select switch 150 may include usage of one or more photosensor(s) or photodetector(s), such that touching, waving, and/or holding finger/hand over the device is operable to select and/or switch between the available measurement modes. This can include light sensors such as photoresistors, photodiodes, phototransistors, etc.

Another embodiment of mode select switch 150 may include usage of a motion sensor, such that moving and/or shaking the device using the hand or finger in a manner which allows the user to select and/or switch between the available measurement modes. This can include any type of motion sensors such as accelerometers, gyro, proximity sensor, etc.

Another embodiment of mode select switch 150 may include usage of a proximity sensor, such that touching, waving and/or holding the finger/hand or other object near the device acts to select a desired operating mode of electronic thermometer 100. This can includes any type of proximity sensors.

Another embodiment of mode select switch 150 may be an audible detector, such that speaking to the electronic thermometer 100 or providing a specific sound such as a clicking sound allows the user to select and/or switch between the available measurement modes. This can include microphones and any other audio/frequency sensors.

A mode selection switch 150 that is actuated by electrical methods (e.g., a touchscreen, photosensor, motion sensor, proximity sensor, audible detector, etc.) may be settable to a desired mode only when electrical power is supplied at least to the mode selection switch 150, for instance by first turning on the electronic thermometer 100.

Another embodiment of switching between the available measurement modes may include usage of a device external to, but in communication with, electronic thermometer 100. In this embodiment, the external device may include any of the embodiments of mode select switch 150 discussed above. The external device then communicates an identification of the selected measurement mode to electronic thermometer 100, and optionally can receive a status or feedback from the electronic thermometer 100. The communication between the external device and the electronic thermometer 100 may be implemented at a physical level by way of wireless communication (RF, Bluetooth, etc) or with wired communication (cable, cradle, etc.).

As discussed above, the electronic thermometer 100 also includes output indicator(s) 151a and/or 151b which provides an output feedback indicator to the patient, attendant, etc. indicating whether the patient's temperature is within certain predetermined ranges (e.g., "normal", "fever," "high fever") depending upon the selected measurement mode.

In one embodiment, the output indicator 151a may include an LED or light source to provide user feedback during measurement mode selection or when displaying a final temperature reading corresponding to a desired measurement mode.

In one embodiment, the output indicator 151b may include graphic and/or text included in the LCD 120, or color (backlight) shown on the product display, to communicate measurement mode selection or when displaying a final temperature reading corresponding to a desired measurement mode.

In one embodiment, the output indicator 151a may include a shape molded, embossed, or otherwise attached to the product housing in order to communicate the measurement mode selection. For instance, if a separate light source is provided to indicate the status of a respective measurement mode, then a shape may be molded on a surface of the electronic thermometer adjacent or near to the respective light source.

In one embodiment, the output indicator 151a may include an audible feedback to communicate the measurement mode selection or when displaying final temperature reading corresponding to a desired measurement mode. The audible feedback may include any type of sound such as beeps, songs, and word(s) in a desired language. The words, for instance, may say "infant," "toddler," "adult," etc. Any characteristic of the audible feedback can be varied, for instance tone/beep/buzz etc., number of the same, duration, loudness, repetition, frequency, chirp, etc. Characteristics perceived as more alarming can be used for more severe measured conditions.

In one embodiment, the output indicator 151a may include mechanical feedback (e.g., vibration). The mechanical feedback may include mechanical movement by the thermometer to communicate the measurement mode selection or when displaying final temperature reading corresponding to a desired measurement mode. Characteristics of the feedback such as frequency, duration, intensity, repetition, delay between repetitions, etc. can be useful to mechanically communicate the measurement mode.

In one embodiment, the light emitting element 124 is capable of generating different colored light to backlight the display 106. For example, the light emitting element 124 can generate a first, second, third, and fourth color. The first color can be white and is illuminated once the power/initialization button 117 is pressed. The power initialization button 117 activates the thermometer 100 or resets it for another reading. The first color of the light emitting element 124 can indicate that the thermometer 100 is ready to read a temperature. The second color, which in an embodiment is green, can correspond to a measurement mode-dependent temperature range that corresponds to a "normal" temperature range for the selected measurement mode.

The third color emitted by the light emitting element 124 can be yellow and can indicate that the patient has a low fever and is "warmer" than normal for the selected measurement mode. The fourth color, which can be red, indicates a high fever for the selected measurement mode.

Alternately, the first through fourth colors can be generated by individual light emitting elements, each generating a separate color, or by combining colors to generate the first through fourth color.

Further, the thermometer 100 can use various routines or algorithms to determine the temperature of the patient, such as a "peak and hold" and a "predictive" algorithm, both of which are described below. The activation of the backlight emitting element 124 of the display 106 can be separate from or linked to the temperature determining routine. Typical routines take constant or intermittent readings from the temperature sensing element 102, apply an algorithm to these readings, and send a display of a sensed temperature Ts once the algorithm has determined that a temperature of the patient has been determined.

Figure 2:
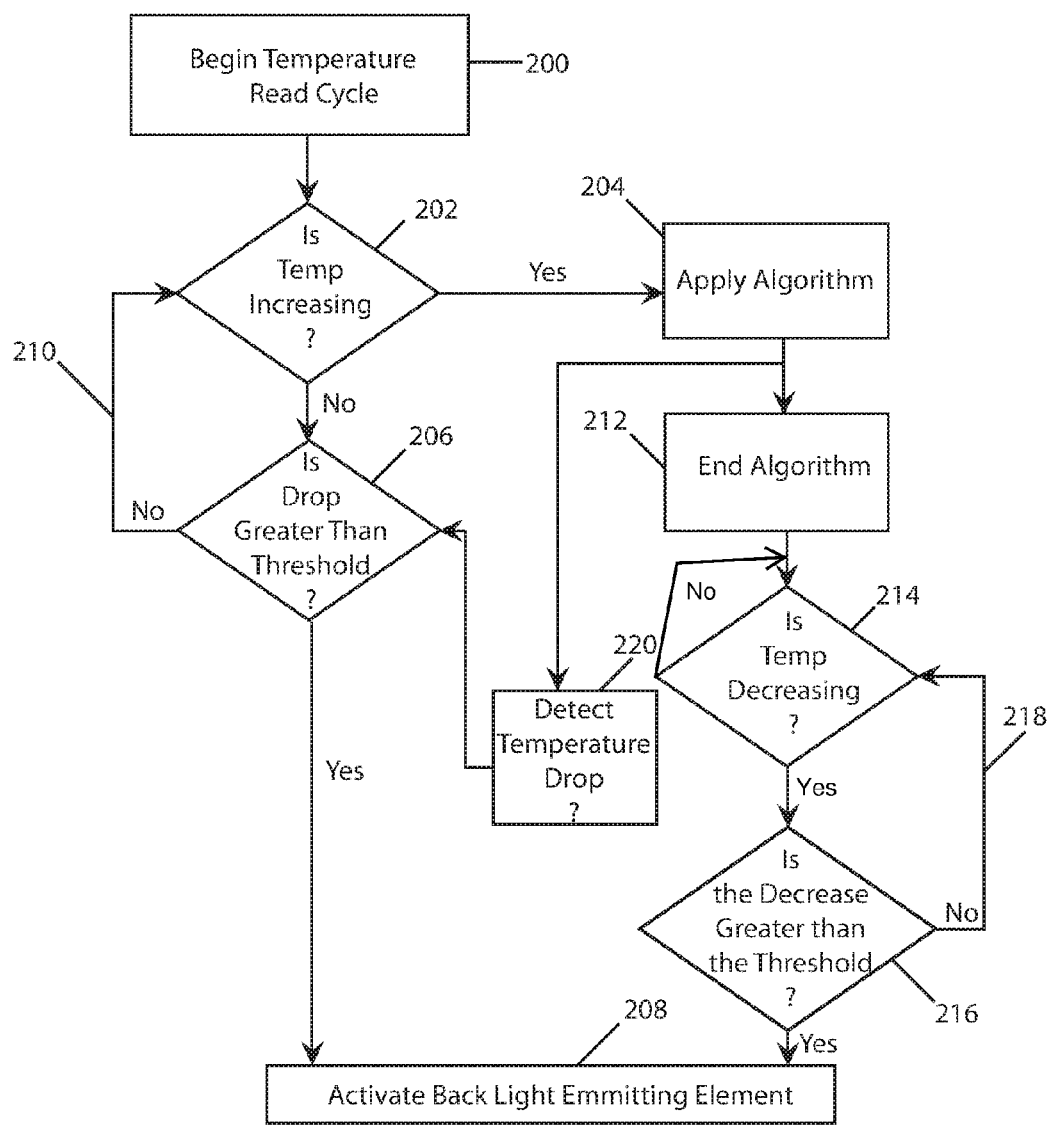
FIG. 2 is a flow diagram illustrating a method to illuminate a backlight of the present invention.

FIG. 2 illustrates a method to activate the backlight emitting element 124. The thermometer 100 can begin the temperature reading cycle (step 200) and the processor 104 can take the readings from the temperature sensing element 102. The processor can look for a temperature increase (step 202) and if a temperature increase is detected, it applies the algorithm to the readings (step 204). If the processor 104 detects a temperature decrease, it determines if the decrease is greater than or equal to a preprogrammed threshold (step 206). If the temperature drop is greater than or equal to the preprogrammed threshold, the processor 104 activates the backlight emitting element 124 (step 208). The reason for activating the light emitting element 124 when a temperature drop meets or exceeds the predetermined threshold, is that this is an indicator that the thermometer has been removed from the patient. When the thermometer is removed from the patient, the thermometer typically undergoes a temperature drop since it is going from the relatively warm body environment to the relatively cooler air outside the body. If the temperature drop is not greater than or equal to the threshold, the processor 104 continues to take readings (step 210) to determine if the temperature is increasing or decreasing.

Alternatively, once the algorithm is complete (step 212), the processor looks for a decrease in temperature (step 214) and if the temperature drop is greater than or equal to the preprogrammed threshold (step 216), the processor 104 activates the backlight emitting element 124 (step 208). If the temperature drop is not greater than or equal to the threshold, the processor 104 continues to take readings (step 218) to determine if the temperature is decreasing.

Additionally, the patient may remove the thermometer in the middle of a temperature read. If this occurs, the processor 104 detects that the temperature which was increasing is suddenly decreasing (step 220) and can interrupt the algorithm to make the threshold determination (step 206) and activate the backlight emitting element 124 (step 208). In a further embodiment, the processor 104 waits a predetermined amount of time after the readings have dropped (for example, 6, 16, or 32 seconds) before beginning to check for the threshold in order to turn on the backlight emitting element 124.

In one embodiment, the temperature sampling routine can implement a "peak and hold" algorithm based on the temperatures indicated by the temperature sensing element 102. The temperature measured by the temperature sensing element 102 must remain stable within a fixed temperature range over a time period. For example, the temperature reading must stay within 0.1° F. for a minimum of 10 seconds. It is to be appreciated by those skilled in the art that other stability windows could also be used to determine that the measurement is stable.

Another temperature sampling routine can be a "predictive" algorithm. This algorithm looks not only at the temperature increase, but at how fast the temperature is increasing. Using change in time and temperature (e.g., the slope of a time vs. temperature curve), the processor 104 can determine what the final temperature should be and display that temperature instead of waiting for the readings to actually reach the final temperature. The backlight activation method of the present invention can be incorporated into either algorithm.

The preprogrammed threshold can be based on temperature, time, or number of readings. The temperature threshold can be if the temperature drops between about 0.1 to about 5° (either Fahrenheit or Centigrade). In one embodiment, the threshold temperature amount is about 0.1° Alternately, the threshold can be determined based on the amount of time it takes to achieve a significant drop in temperature without having the patient wait too long for the backlight to activate. This time can vary between about 1 to about 6 seconds.

Further, the threshold can be the number of readings in which the temperature drops. The number of readings can vary between 1 and about 10,000, depending on the sampling rate of the thermometer and the length of time the thermometer is sampling. Thus, if the processor reads one or more temperatures where the current reading decreases from the previous reading, the backlight is triggered.

In another embodiment, the backlight may be activated prior to the detection of a sufficient temperature drop. For instance, the backlight may be activated when the temperature readings plateau, or when the rate of increase of the temperature readings drops below a predetermined positive rate, or when the "predictive" algorithm has determined the final temperature. This may correspond to a time when the temperature measurement is substantially completed, and/or a time when the thermometer has been removed, prior to the occurrence of a sufficient drop in temperature. Such an early activation of the backlight may also serve as an indicator to the patient or an attendant that the measurement is completed and that the thermometer may be removed from the measurement location. Other completion indicators may also be used, such as beeps, etc.

In another embodiment, such algorithmic activation of the backlight may be combined with a human-controllable switch to allow for manual activation of the backlight. Manual activation may be desirable if, e.g., the patient or attendant wants to view the current measured temperature in order to estimate the remaining time until completion of the temperature measurement.

FIGS. 3A-3D illustrate another embodiment of the thermometer 300. A temperature sensing element 302 is connected to a powered processor 304 and/or a display 306. The components are housed in a case 308 having a probe section 310 and a body section 312. The body section 312 can include an output mode indicator 350 (similar to that of FIG. 1), a power/initialization button 317 and the temperature sensing element 302 is mounted at the end of probe section 310.

The processor 304 can receive signals from temperature sensing element 302 related to the temperature of the patient. The processor 304 can convert the signals to a temperature in either Fahrenheit or Centigrade. The processor 304 can also include a memory 318 for storing ranges of temperatures and can compare the currently read temperature to the stored temperatures to determine which element of display 306 to illuminate. The memory 318 can also store one or more previously read temperatures. In an embodiment, memory activation button 332 can be depressed after a reading to store the reading and can be depressed afterwards to recall the stored reading and cycle through numerous other stored readings.

The display 306 can include a translucent liquid crystal display (LCD) 320. LCD 320 can be any shape, including rectangular and octagonal and can be a "reverse" LCD. A reverse LCD lights the numerals of the display instead of the background. This increases the visibility and viewing angle of the LCD 320.

The display 306 can further include a transparent or translucent lens 322. In an embodiment, the lens 322 can be circular, elliptical, or any other shape to form the display 306. One or more lighting elements 324, e.g., LEDs, are disposed in the display 306 and peripheral to LCD 320. The light emitting element 324 edge lights the display 306 to illuminate the LCD 320.

Figure 3A:
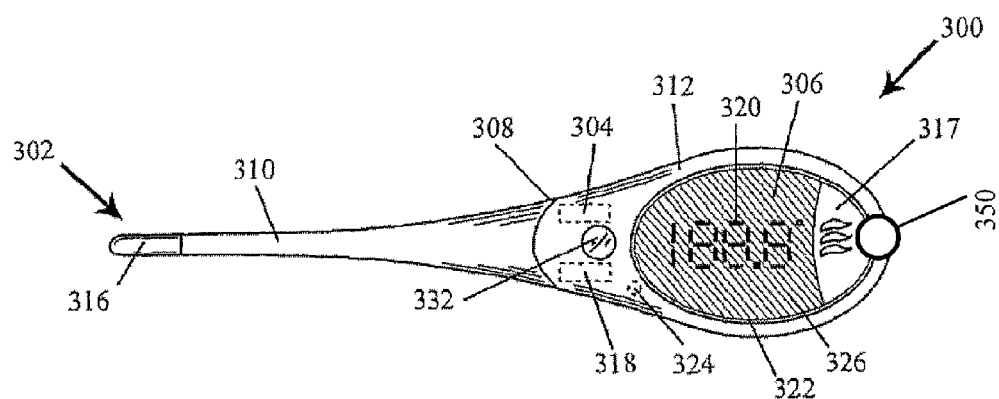
FIGS. 3A-3D are top views of an embodiment of a color display thermometer of the present invention in different stages of illumination.
Figure 3B:
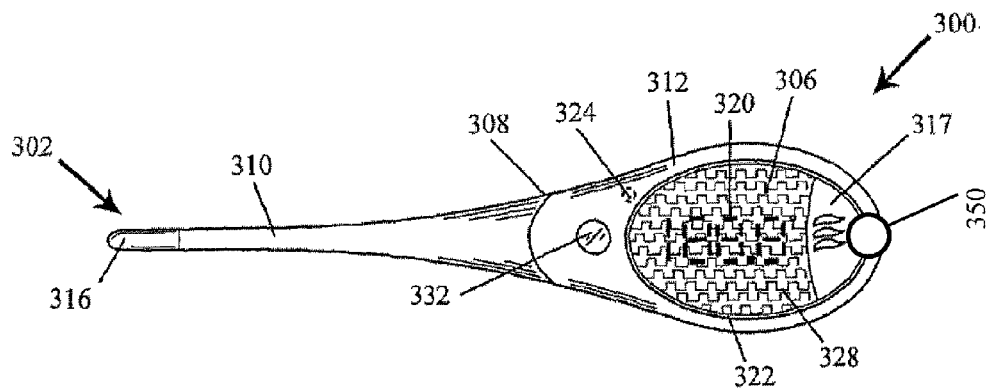
Figure 3C:
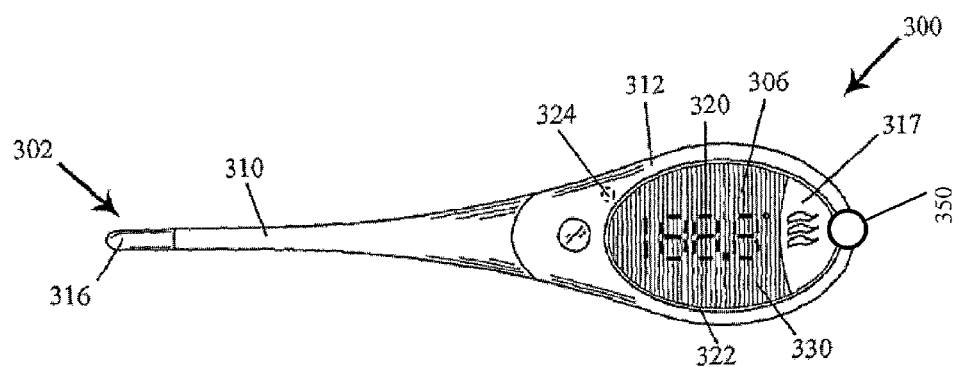
Figure 3D:
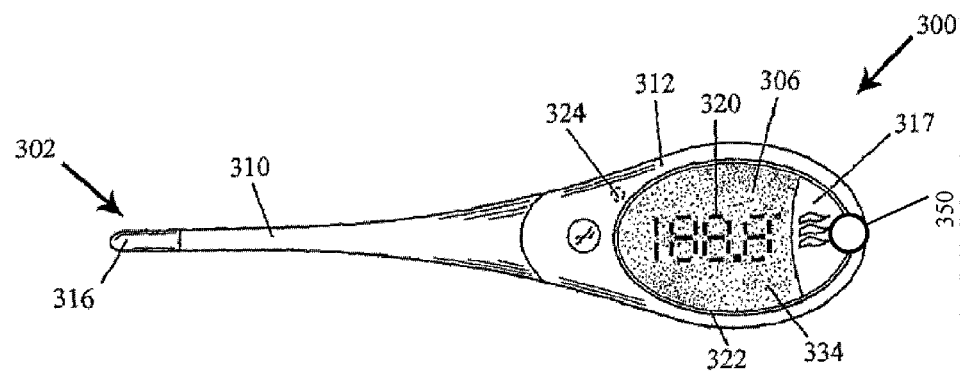

In one embodiment, using only FIGS. 3A-3C the light emitting element 324 is capable of generating different colored light to edge light the display 306. For example, the light emitting element 324 can generate a first, second, and third color. The first color 326, illustrated in FIG. 3A, which in an embodiment is green, can correspond to a range of temperatures indicating a "normal" temperature of the patient. The second color 328 emitted by the light emitting element 324 can be yellow and can indicate that the patient is "warmer" than normal, as illustrated in FIG. 3B. FIG. 3C illustrates the third color 330, which can be red, and indicates a fever. The temperature range corresponding to each of the first, second and third colors, respectively can be dictated by the preferred location to read the temperature of the patient and the age of the patient. Different age groups of patients as well as whether the temperature is taken orally, rectally, or axillary can dictate different ranges of temperatures considered normal, warm and fever. Additionally, more than one light emitting element can correspond to the chosen temperature range or multiple light emitting elements can be illuminated at one time. Each color can be a separate light emitting element, one element can emit all of the colors, or combinations of light emitting elements can form one or more colors.

In another embodiment, using FIGS. 3A-3D, the light emitting elements 324 are capable of generating a first, second, third, and fourth color. The first color 326 can be white and is illuminated once the power/initialization button 317 is pressed. The power initialization button 317 activates the thermometer 300 or resets it for another reading. The first color 326 of the light emitting elements 324 can indicate that the thermometer 300 is ready to read a temperature. Further, the first color 326, which in an embodiment, can be white, can indicate an incomplete reading was taken from the fact that the sensed temperature Ts is less than 97° F. The second color 328, which in an embodiment is green, can correspond to temperatures ranging between 97-98.9° F. Thus, the second color can indicate a "normal" temperature of the patient.

The third color 330 emitted by the light emitting elements 324 can be yellow and can indicate that the patient is "warmer" than normal. A typical "warm" temperature range is 99.0-100.9° F. The fourth color 334, which can be red, indicates a fever where the temperature of the patient is greater than 101.0° F.

Alternately, the first through fourth colors 326, 328, 330, 334 can be generated by individual light emitting elements, each generating a separate color, or by combining colors to generate the first through fourth colors.

FIG. 4 illustrates the method of activating the backlight emitting elements for an exemplary four color scheme. Thermometer 300 can use various temperature sampling routines to determine the temperature of the patient, including the "peak and hold" and "predictive" routines described above. The activation of the light emitting elements 324 to illuminate the display 306 can be separate from or linked to the temperature sampling routine.

The method includes the thermometer 300 lighting the first color 326 to indicate that the thermometer 300 is ready to read a temperature from the temperature sensing element 302 (step 400). In one embodiment, the first color 326 can remain illuminated throughout the entire read cycle. However, certain thermometers do not have enough battery power to keep the light emitting elements 324 illuminated at the same time a reading is being taken. If battery power is an issue, the first color 326 light emitting element 324 can be shut off after a specific amount of time or once the temperature reading is begun. The temperature reading cycle begins (step 402) and the processor 304 can take the readings from the temperature sensing element 302. The processor 304 applies an algorithm (step 404) and looks for a temperature change (step 406). If the temperature is increasing or steady, the processor 304 determines if the temperature reading has ended (step 408) and may continue to apply the algorithm (step 410). If the processor 304 detects a temperature decrease, it determines if the decrease is greater than a preprogrammed threshold (step 412). If the temperature drop is greater than to equal to the preprogrammed threshold, the processor 304 activates the first color 326 (step 414). If the temperature drop is not greater than or equal to the threshold, the processor 304 continues to take readings (step 416) to determine if the temperature is increasing or decreasing.

Once the algorithm has ended, the processor 304 determines the sensed temperature Ts (step 418). Then the processor 304 looks for a decrease in temperature (step 420) and if the temperature drop is greater than or equal to a preprogrammed threshold (step 422). The processor 304 compares the sensed temperature Ts to a first range (step 424) and if the sensed temperature falls within the first range, the second color 328 is illuminated (step 426). If the sensed temperature Ts does not fall within the first range, the processor 304 determines if it falls within a second range (step 428), and if so, illuminates the third color 330 (step 430). If the sensed temperature Ts does not fall within the second range, the processor 304 determines if it falls within a third range (step 432), and if so, illuminates the fourth color 334 (step 434). If the sensed temperature Ts does not fall within the three ranges, the first color can be illuminated (step 436).

For example, when a patient activates the thermometer, a white light emitting element can be activated. The processor starts a temperature read and can optionally turn off the white light emitting element. If the patient removes the thermometer in the middle of the temperature read, the processor detects the decrease in temperature and activates the white light emitting element. If the patient leaves the thermometer in place until the temperature reading is complete, the processor then waits to detect a temperature decrease. Once the patient removes the thermometer from the temperature sensing position, the temperature of the temperature sensing element drops, which is detected by the processor. The processor detects the drop and determines if the drop is larger than or equal to the preprogrammed threshold. If the drop matches the threshold, the processor determines if the sensed temperature falls within the above-discussed predetermined ranges. The processor then illuminates either the green, yellow, or red light emitting element depending on which range the sensed temperature falls into.

In a further embodiment, the processor waits a predetermined amount of time after the readings have dropped (for example, 6, 16, or 32 seconds) before beginning to check for the threshold temperature drop.

The preprogrammed threshold can be based on temperature, time, or number of readings. The temperature threshold can be if the temperature drops between about 0.1 to about 5° (either Fahrenheit or Centigrade). In one embodiment, the threshold temperature amount is about 0.1°. Alternately, the threshold can be determined based on the amount of time it takes to achieve a significant drop in temperature without having the patient wait too long for the backlight to activate. This time can vary between about 1 to about 6 seconds.

Further, the threshold can be the number of readings in which the temperature drops. The number of readings can vary between 1 and about 10,000 depending on the sampling rate of the thermometer and the length of time the thermometer is sampling. Thus, if the processor reads one or more temperatures where the current reading decreases from the previous reading, the light emitting element is triggered.

Figure 11:
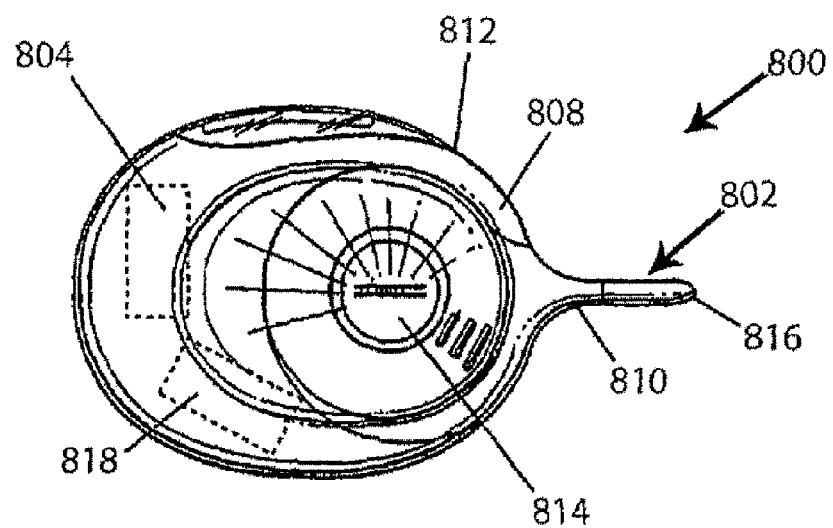
FIG. 11 is a right side view of a further embodiment of a color display thermometer of the present invention.
Figure 12:
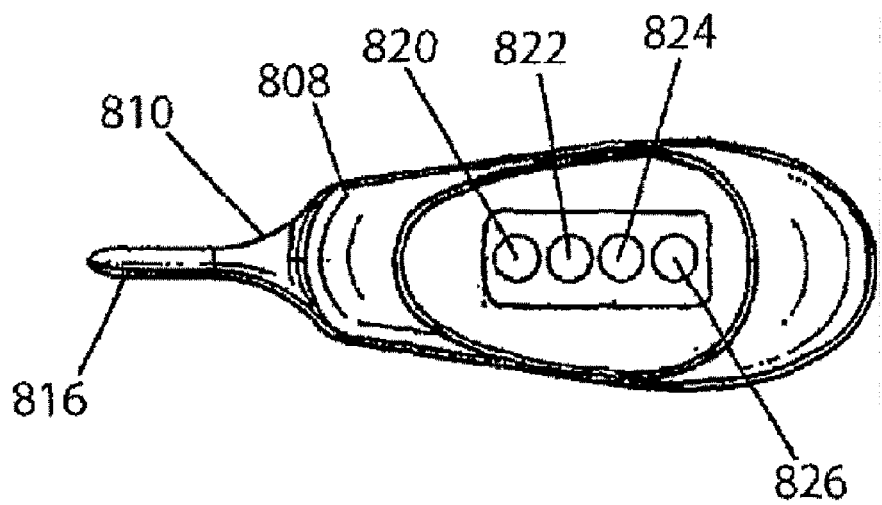
FIG. 12 is top view of the embodiment illustrated in FIG. 11.

Referring to FIGS. 11 and 12, an embodiment of an electronic thermometer 800 for use with a living being is illustrated. A temperature sensing element 802 is connected to a powered processor 804 and/or a display 806. The components are housed in a rigid plastic case 808 having a probe section 810 and a body section 812.

The processor 804 and display 806, and in one embodiment a battery (not illustrated), are secured in the body section 812 of rigid case 808 along with an access door 814, optionally provided for battery replacement. Further, body section 812 can include a power/initialization button (not illustrated). Temperature sensing element 802 is mounted at the end of probe section 810 and covered with a conductive cap 816.

Processor 804 can receive signals from temperature sensing element 802 related to the temperature of the living being, i.e., the patient. Processor 804 can convert the signals to a temperature in either Fahrenheit or Centigrade. The processor 804 can also include a memory 818 for storing ranges of temperatures and corresponding colors for the display 806. Processor 804 can compare the currently read temperature to the stored temperatures and corresponding colors to determine which element of display 806 to illuminate.

Display 806 includes multiple lighting elements, which in an embodiment, can be light emitting diodes (LEDs) or similar light emitting elements. In one embodiment, illustrated in FIGS. 11 and 12, the first light emitting element 820, is a first color. A second light emitting element 822 is a second color, a third light emitting element 824 is a third color and a fourth light emitting element 826 is a fourth color.

In one embodiment, the first color of the first light emitting element 820 can be white and is illuminated once the power/initialization button is pressed. The power initialization button activates the thermometer 800 or resets it for another reading. The first light emitting element 820 can indicate that the thermometer 800 is ready to read a temperature. Second light emitting element 822 can illuminate a second color, which in an embodiment is green. The temperature corresponding to the second color can be temperatures ranging between 97-98.9°. F. Thus, the second color can indicate a "normal" temperature of the patient.

The third color emitted by the third light emitting element 824 can be yellow and can indicate that the patient is "warmer" than normal. A typical range is 99.0-100.9° F. The fourth light emitting element 826 can have the fourth color of red indicating a fever where the temperature of the patient is greater than 101.0° F.

In use with a rectal thermometer embodiment, the user presses the power/initialization button and waits for the first light emitting element 820 to light indicating that thermometer 800 is ready to read a temperature. The user places probe section 810 and the tip 816 in contact with the patient's rectal region, and within the anal canal, to sense the temperature thereof. As the processor 804 receives the temperature signal, it accesses memory 818 to determine the range in which the read temperature falls. Processor 804 then intermittently lights second light emitting element 822 as the temperature is being read. The flashing second light emitting element 822 indicates that the reading is not complete. Once the reading is complete, second light emitting element 822 can be illuminated steadily, indicating to the user that the reading is complete and that the temperature of the patent falls within the "green" range.

If the temperature of the patient increases during the reading, the third or fourth light emitting elements 824, 826 can also be intermittently lit. Thus, the third light emitting element 824 can flash and steadily illuminate the third color while the reading is within the range calibrated for the third color. Further, if the temperature of the patient dictates, the fourth light emitting element 826 can flash and then turn steady to indicate that the reading is complete and the patient has a fever. Thus, as the reading is being taken, the light emitting elements transition from the first to the fourth color while flashing and then steadily illuminate the light emitting element corresponding to the actual temperature of the patient.

In alternate embodiments, the processor 804 starts by lighting the first light emitting element 820 in one of a steady or intermediate fashion and just lights a designated light emitting element 822, 824, 826 as dictated by the final temperature of the patient. The light emitting element is illuminated in a steady state to only indicate the final actual temperature of the patient.

Figure 5:
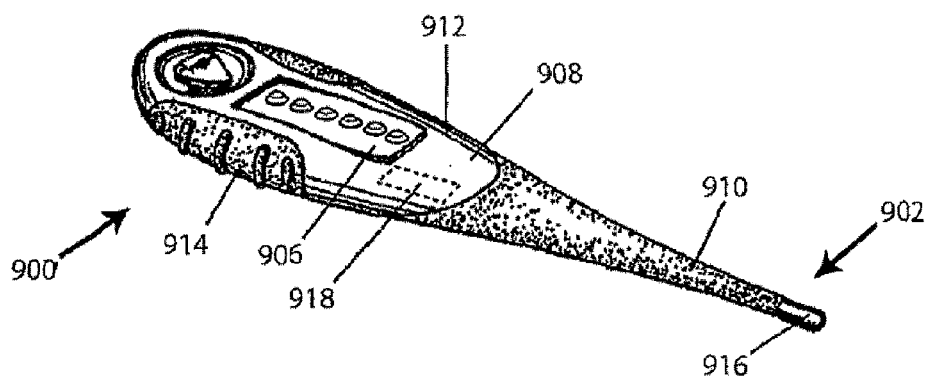
FIG. 5 is a perspective view of another embodiment of the color display thermometer of the present invention.
Figure 6:
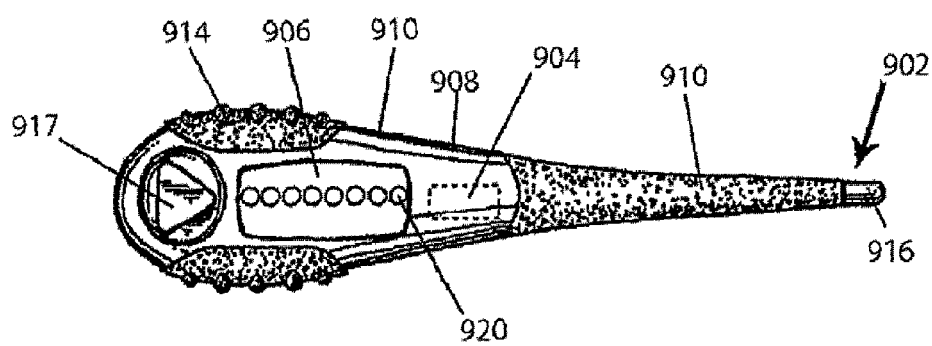
FIG. 6 is a top view of the embodiment of FIG. 5.
Figure 7:
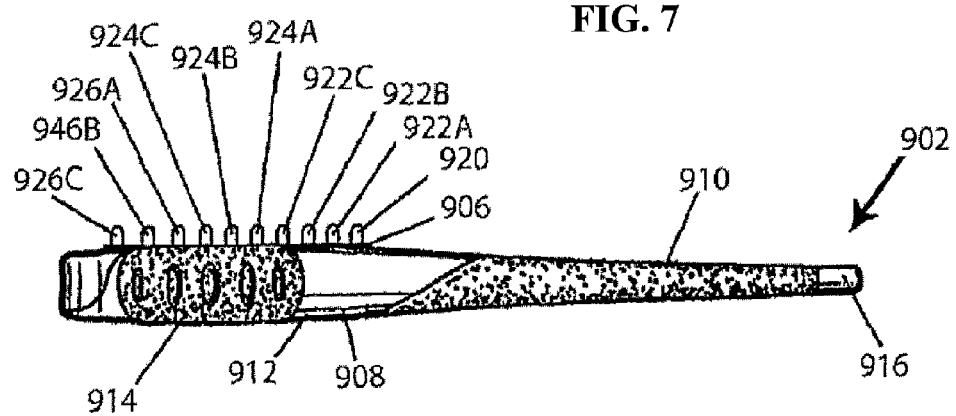
FIG. 7 is a right side view of the present invention as illustrated in FIG. 5.

Referring to FIGS. 5-7, another embodiment of an electronic thermometer 900 for use with a living being is illustrated. A temperature sensing element 902 is connected to a powered processor 904 and display 906. The components are housed in a case 908 (typically rigid plastic) having a probe section 910 and a handle section 912. Handle section 912 can include a grip 914.

Temperature sensing element 902 is mounted at the end of probe section 910 and covered with a conductive cap 916 (typically metal, e.g. nickel or stainless steel). The processor 904 and display 906, and in one embodiment a battery (not illustrated), are secured in the handle section 912 of rigid case 908 along with an access door, optionally provided for battery replacement (not illustrated). Further, handle section 912 can include a power/initialization button 917.

Processor 904 can receive signals from temperature sensing element 902 related to the temperature of the patient. Processor 904 can convert the signals to a temperature in either Fahrenheit or Centigrade. The processor 904 can also include a memory 918 storing ranges of temperatures and corresponding colors for display 906. Processor 904 can compare the currently read temperature to the stored temperatures to determine which element of display 906 to illuminate.

Display 906 includes multiple lighting elements, which in an embodiment, can be light emitting diodes (LEDs) or similar light emitting elements. In one embodiment, illustrated in FIGS. 5-7, the first light emitting element 920, is a first color. Second light emitting elements 922A-922C are a second color, third light emitting elements 924A-924C are a third color and fourth light emitting elements 926A-926C are a fourth color.

In an embodiment, the first color of the first light emitting element 920 can be white and is illuminated once the power/initialization button 917 is pressed. The first light emitting element 920 can indicate that the thermometer 900 is ready to read a temperature. Second light emitting elements 922A-922C can illuminate a second color, green. The temperature corresponding to the second color can be temperatures ranging between 97-98.9° F. The temperature range can be divided evenly across the second light emitting elements 922A-922C wherein second light emitting element 922A corresponds to a range of 97-97.6° F., second light emitting element 922B corresponds to a range of 97.7-98.3° F., and second light emitting element 922C corresponds to a range of 98.4-98.9° F. A second color can indicate a "normal" temperature of the patient. The third color can be yellow and can indicate that the patient is "warmer" than normal. A typical range for the third color is 99.0-100.3° F.

and can again be divided between the third light emitting elements 924A-924C. Fourth light emitting elements 926A-926C can have the fourth color of red. This can indicate a fever and a range of 100.4 to greater than 101.0° F.

In use with an oral thermometer embodiment, the user presses power/initialization button 917 and waits for the first light emitting element 920 to light. In an embodiment, once the white light is lit, the thermometer 900 is ready to read a temperature. The user places the probe section 910 in the patient's mouth and disposes the tip 916 with temperature sensing element 902 under the patient's tongue to begin reading the patient's temperature. As the processor 904 receives the temperature signal it accesses memory 918 to determine the temperature ranges, compares the read temperature against the ranges, and determines which light emitting element to illuminate. Processor 904 then can incrementally light second light emitting elements 922A-922C as the temperature increases. If the temperature of the patient increases, the third and fourth light emitting elements 924A-924C and 926A-926C may also be incrementally lit. Processor 904 determines that the final temperature of the patient is reached and the light emitting element corresponding to the final temperature range cane illuminated steadily or blinks to indicate that the reading is complete.

Embodiments include changing the color scheme to be any range of colors. Alternately, all of the first through fourth light emitting elements can be one element capable of emitting a range of colors. The light emitting elements of the oral thermometer 900 embodiment can be differing shades of the same base color. For example, second light emitting element 922A can be a darker green than second light emitting element 922C. The same shading scheme can be used for third and fourth light emitting elements 924A-924C and 926A-926C. Further, multiple light emitting elements can be illuminated to form the necessary colors. An embodiment can utilize a color scale of blue, green and yellow, where blue and yellow light emitting elements illuminate to form the green color in the display. Further, intensities of certain base colors can be used to form any and every color. For example, combinations of red, blue and green can form many colors of the spectrum and these base colors can be used solely to be combined to form the first through fourth colors of the above embodiments. The base colors themselves may not be a color in the selected range.

Figure 8:
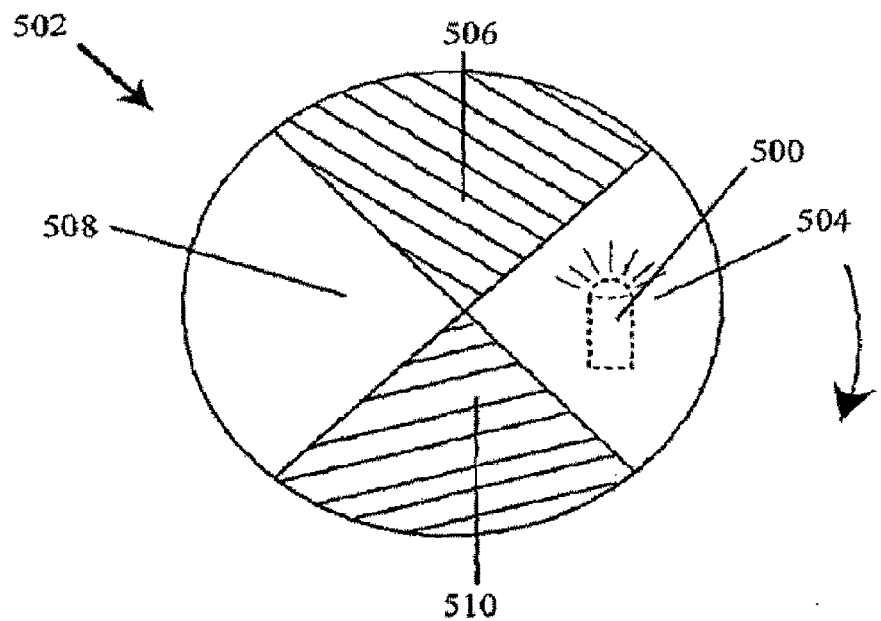
FIG. 8 is an embodiment of a display element of the present invention.

FIG. 8 illustrates an embodiment of the display 306/806/906. A single light emitting element 500 can be illuminated, either steadily or intermittently, and a colored filter 502 can be passed over the light emitting element 500 to display varying colors. For example, single light emitting element 500 can emit white light and colored filter 502 can have a clear portion 504, a first color portion 506 (e.g., green), a second color portion 508 (e.g., yellow) and a third color portion 510 (e.g., red).

Figure 9:
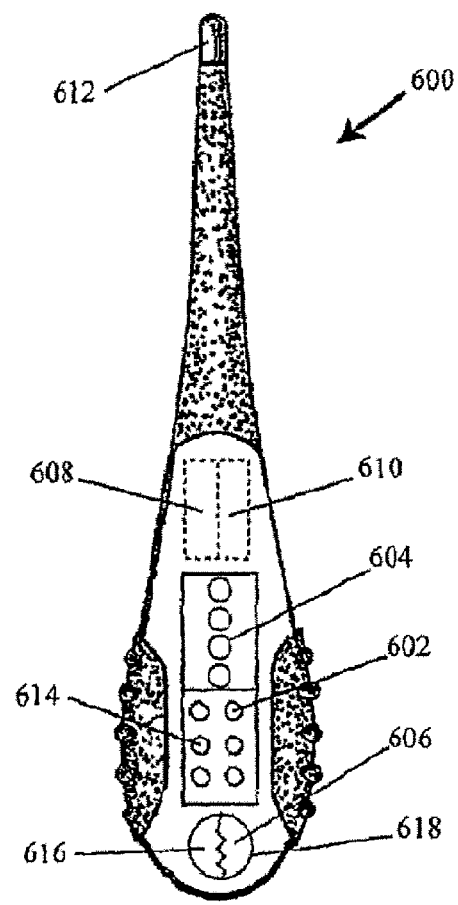
FIG. 9 is a top view of a further embodiment of the present invention.

FIG. 9 illustrates another embodiment of thermometer 600. Thermometer 600 can include many of the elements of the previous thermometers 100, 200, 300, 400 and can also include a patient adjustment scale 602 as part of or in addition to temperature display 604. Patient adjustment button 606 can be depressed to cycle between, for example, infant, child and adult temperature ranges. Thus, the ranges stored in memory 608 and accessed by processor 610 can vary by age of the patient. Thus, the user can change the set-points of the light emitting elements based on the age of the patient.

A further embodiment can change the set-points stored in memory 608 based on the placement of the temperature probe 612. A location display 614 can indicate where the user intends to place the thermometer to read the patient's temperature. Different temperature readings indicate a fever at different locations on the patient. For example, a temperature of 100.4° F. (38° C.) measured rectally corresponds to 99.5° F. (37.5° C.) measured orally which corresponds to a temperature of 99° F. (37.2° C.) measured in an axillary position. Location adjustment button 616 can be depressed to cycle through the available options for location.

Alternate embodiments include depressing only power/initialization button 918 to select all adjustment options and having just patient and location adjustment buttons 906, 916 as incremental switches without a corresponding display 902, 914. Additionally, all options, including temperature, patient, and location can be displayed using only one display to alternately display each set of options. Further, in an embodiment, only the display for the patient or location options can be an LCD display. Furthermore, the temperature ranges are exemplary only and can be changed to any given range.

Figure 10A:
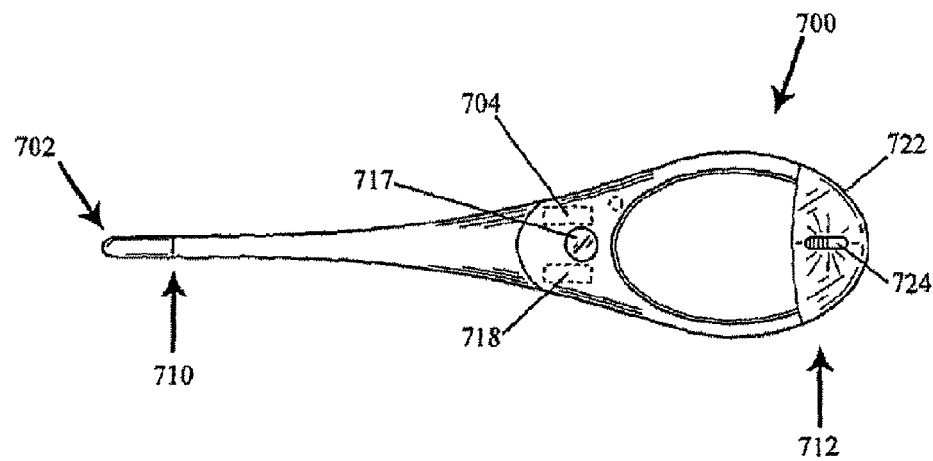
FIGS. 10a and 10b are perspective views of an additional embodiment of the present invention.
Figure 10B:
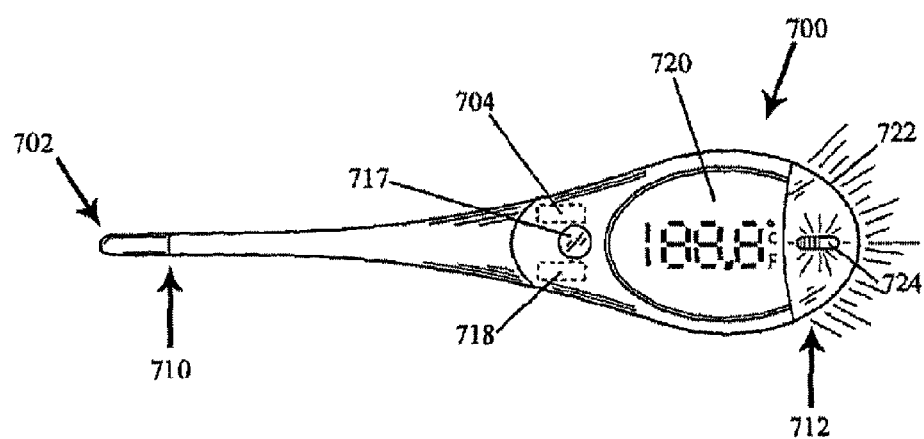

FIGS. 10a and 10b illustrate another embodiment of an electronic thermometer 700. A temperature sensing element 702 is connected to a powered processor 704 and/or a display 706. The components are housed in a plastic case 708 having a distal end 710 and a proximal end 712. The proximal end 712 can include a power/initialization button 717 and the temperature sensing element 702 is mounted at the distal end 710.

The processor 704 can receive signals from temperature sensing element 702 related to the temperature of the patient. The processor 704 can convert the signals to a temperature in either Fahrenheit or Centigrade. The processor 704 can also include a memory 718 for storing ranges of temperatures and can compare the currently read temperature to the stored temperatures to determine which element of display 706 to illuminate. The memory 718 can also store one or more previously read temperatures.

The display 706 can include a transparent or translucent lens 722 disposed on the proximal end 712. In one embodiment, the lens 722 is disposed at the far proximal end. Also, in an embodiment, the lens 722 can be circular, elliptical, or any other shape to form the display 706. One or more lighting elements 724, e.g., LEDs, are disposed in the display 706 and under lens 722.

In an embodiment illustrated in FIG. 10b, the display 706 can also include a translucent liquid crystal display (LCD) 720. LCD 720 can be any shape, including rectangular and octagonal and can be a "reverse" LCD. A reverse LCD lights the numerals of the display instead of the background. This increases the visibility and viewing angle of the LCD 720. The LCD can be used to display the actual temperature reading. The LCD 720 can be peripheral to lens 722.

In one embodiment, the light emitting element 724 is capable of generating different colored light to light the display 706. For example, the light emitting element 724 can generate a first, second, and third color. The first color can be green to correspond to a "normal" range of temperatures of the patient. The second color can be yellow and indicate a "warmer" than normal temperature. The third color can be red to indicate a fever.

Other embodiments can use elements from any of the above embodiments with elements of the other embodiments. For example, thermometer 900 an have a memory to store previous temperature reading, thermometers 100, 300, 800 can have patient and location options, and any of the displays can optionally display the actual temperature or only display the colors of the light emitting elements.

Further embodiments include sequentially lighting the display. Thus, as the temperature is being taken, the first light emitting element is illuminated, and remains illuminated even as the second light emitting element is illuminated. This pattern continues until all the light emitting elements are illuminated or the temperature of the patient is reached. Thus, the last light emitting element lit indicates the temperature, while the previous light emitting elements remain lit. In an alternate embodiment, the light emitting element is illuminated when the temperature reading corresponds to that element and then is turned off as the next light emitting elements is illuminated based on the corresponding temperature reading.

Additionally, in the embodiments having both an LCD and light emitting elements, the processor can read the temperature from the temperature sensing element and display the temperature on both the LCD and light emitting elements and illuminate the light emitting elements independent of the display on the other. Thus, the light emitting elements can be illuminated based solely on the temperature reading and not based on the reading displayed on the LCD. Thus, this acts as a failsafe wherein if one display is damaged the other can still display an accurate temperature. Alternately, the illumination of the light emitting elements can be based on the temperature displayed on the LCD. This removes the possibility of an inconsistent display wherein the LCD displays a temperature and a light emitting element that does not correspond to that temperature is illuminated. Furthermore, an embodiment only flashes the light emitting elements, the LCD display does not flash in response to the temperature ranges. The LCD can flash to indicate that the temperature is being read, or alternately, that the reading is complete. However, the flashing of the LCD is not related to the magnitude of the temperature being read.

Further embodiments place the light emitting elements anywhere in body section of the thermometer to illuminate the face of the display, including the LCD. Also, an embodiment has both an LCD and light emitting elements in the display, but the elements are separate so that the LCD displays the temperature and is not illuminated by the light emitting elements and the light emitting elements illuminate separate from the LCD.

Additional embodiments include continuously updating which light emitting element to illuminate as the temperature is being read. Thus, as the temperature of the patient is being taken, the light emitting elements can be correspondingly or sequentially lit until the final light emitting element is illuminated in response to the final temperature. Alternately, the light emitting element is not lit until the final temperature reading is determined.

Embodiments can include changing the color scheme to be any range of colors. Alternately, all of the light emitting elements can be one element capable of emitting a range of colors. The light emitting elements can be differing shades of the same base color. For example, the second color can be a darker green than first color. The same shading scheme can be used for third and fourth light emitting elements.

Further, multiple light emitting elements can be illuminated to form the necessary colors. An embodiment can utilize a color scale of blue, green and yellow, where blue and yellow light emitting elements illuminate to form the green color in the display. Further, intensities of certain base colors can be used to form any and every color. For example, combinations of red, blue and green can form many colors of the spectrum and these base colors can be used solely to be combined to form the first through fourth colors of the above embodiments. The base colors themselves may not be a color in the selected range.

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

The invention claimed is:

1. A thermometer for use with a living being, comprising:
 a temperature sensor;
 a processor operable to determine a temperature of the living being based on the temperature sensor, and operable to determine a rate of increase of the determined temperature of the living being;
 a memory coupled to the processor, the memory configured to store information related to a plurality of operating modes;
 a switch configured to select one operating mode from among the plurality of operating modes, to produce a selected operating mode, wherein the selected operating mode comprises at least one temperature range;
 a plurality of first indicators, each corresponding to a respective operating mode;
 a plurality of visual indicators, each corresponding to a respective first indicator; and
 at least one completion indicator configured to indicate determination of the temperature of the living being is substantially completed in response to the processor determining the rate of increase of the determined temperature of the living being is below a predetermined positive rate;
 wherein each of the first indicators when activated, indicating, in conjunction with the corresponding visual indicator, the selected operating mode prior to the processor determining the temperature of the living being.

2. The thermometer of claim 1, wherein the plurality of first indicators comprises a single light source capable of illuminating with a plurality of colors, wherein each color corresponds to one of the first indicators.

3. The thermometer of claim 1, wherein the plurality of first indicators comprises a single light source capable of illuminating with a plurality of intensity levels, wherein each intensity level corresponds to one of the first indicators.

4. The thermometer of claim 1, wherein each of the visual indicators comprises text or graphics.

5. The thermometer of claim 1, wherein selection of the selected operating mode is based upon age of the living being.

6. The thermometer of claim 1, wherein selection of the selected operating mode is based upon a trait of the living being.

7. The thermometer of claim 1, wherein selection of the selected operating mode is based upon a location of the temperature sensor on or in the living being.

8. The thermometer of claim 1, wherein the switch is configured to be a button, the pressing of which cycles through the plurality of operating modes.

9. The thermometer of claim 1, wherein the switch comprises a hall-effect switch.

10. The thermometer of claim 1, wherein the switch comprises a slidable switch.

11. The thermometer of claim 1, wherein the switch comprises a thumbwheel switch.

12. The thermometer of claim 1, wherein the switch is further configured to switch the thermometer on or off.

13. The thermometer of claim 1, further comprising an audible detector to detect an audible signal that is used to actuate the switch.

14. The thermometer of claim 1, the thermometer further comprising an input/output user interface implemented using said display.

15. The thermometer of claim 1, wherein the switch comprises a rotatable switch on a major surface of the thermometer, the switch rotatable within the major surface.

16. The thermometer of claim 1, wherein the switch is operable when the thermometer is off.

17. The thermometer of claim 1, wherein the switch is operable only when the thermometer is on.

18. The thermometer of claim 1, wherein the thermometer further comprises: a housing used to house the processor, the memory and the first indicator in a fixed spatial relationship relative to the housing; and wherein the switch comprises: a slidable portion having a handle operable by a user, and a magnet affixed to the slidable portion; a non-slidable portion in a fixed spatial relationship relative to the housing; and at least one hall element affixed to the non-slidable portion.

19. The thermometer of claim 1, wherein the thermometer further comprises:
  a housing used to house the processor, the memory and the first indicator in a fixed spatial relationship relative to the housing; and
  wherein the switch comprises:
    a slidable portion having a handle operable by a user, and at least one hall element affixed to the slidable portion;
    a non-slidable portion in a fixed spatial relationship relative to the housing; and
    a magnet affixed to the non-slidable portion.

20. The thermometer of claim 1, wherein the thermometer further comprises:
  a housing used to house the processor, the memory and the first indicator in a fixed spatial relationship relative to the housing; and
  wherein the switch comprises:
    a rotatable portion having an arc-shaped bezel operable by a user, and a magnet affixed to the rotatable portion;
    a non-rotatable portion in a fixed spatial relationship relative to the housing; and
    at least one hall element affixed to the non-rotatable portion.

21. The thermometer of claim 1, wherein the thermometer further comprises:
  a housing used to house the processor, the memory and the first indicator in a fixed spatial relationship relative to the housing; and
  wherein the switch comprises:
    a rotatable portion having an arc-shaped bezel operable by a user, at least one hall element affixed to the rotatable portion;
    a non-rotatable portion in a fixed spatial relationship relative to the housing; and
    a magnet affixed to the non-rotatable portion.

22. The thermometer of claim 1, further comprising a proximity sensor to detect a nearby object within a predetermined distance from the proximity sensor, wherein the proximity sensor is configured to actuate the switch when the nearby object is detected.

23. The thermometer of claim 1, wherein the completion indicator comprises at least one lighting element.

24. The thermometer of claim 1, wherein the completion indicator, when activated, backlights the display.

25. The thermometer of claim 1, wherein the completion indicator comprises audible feedback.

26. The thermometer of claim 1, wherein each of the first indicators comprises a light source.

27. The thermometer of claim 26, wherein the light source is an LED.

28. The thermometer of claim 1, wherein the first indicators are provided as part of an output display.

29. The thermometer of claim 28, wherein the output display is an LCD.

30. The thermometer of claim 1, wherein the visual indicators are provided as part of an output display.

31. The thermometer of claim 30, wherein the output display is an LCD.

32. The thermometer of claim 1, wherein the switch comprises a pressure-sensitive detector.

33. The thermometer of claim 32, wherein the switch comprises a touch-sensitive portion of the display.

34. The thermometer of claim 1 further comprising an output display including a light source capable of illuminating with a plurality of colors, wherein each operating mode includes a plurality of temperature ranges, with each temperature range corresponding to a temperature condition of the living being, and each of the plurality of colors corresponding to one of the temperature ranges.

35. The thermometer of claim 34, wherein the light source is an LED.

36. The thermometer of claim 34, wherein the light source is a backlight light source.

37. The thermometer of claim 1, wherein the processor controls the switch based upon a control signal received from a remote device.

38. The thermometer of claim 37, further comprising: a transmitter in communication with the processor, the transmitter configured to transmit a status signal to the remote device.

39. The thermometer of claim 37, wherein the processor receives the control signal using a wireless signal.

40. The thermometer of claim 37, wherein the processor receives the control signal by an electrical contact with the remote device.

41. A system for use with a living being, comprising:
  a thermometer; and
  a control unit external to the thermometer and in communication with the thermometer,
  wherein the thermometer comprises:
    a temperature sensor;
    a processor operable to determine a temperature of the living being based on the temperature sensor, and operable to determine a rate of increase of the determined temperature of the living being;

a memory coupled to the processor, the memory configured to store information related to a plurality of operating modes;

a switch configured to select one operating mode from among the plurality of operating modes, to produce a selected operating mode, wherein the selected operating mode comprises at least one temperature range;

a plurality of first indicators, each corresponding to a respective operating mode;

a plurality of visual indicators, each corresponding to a respective first indicator;

at least one completion indicator configured to indicate determination of the temperature of the living being is substantially completed in response to the processor determining the rate of increase of the determined temperature of the living being is below a predetermined positive rate;

a receiver configured to receive a control signal sent to the thermometer; and a transmitter configured to send a status signal from the thermometer;

wherein each of the first indicators when activated, indicating, in conjunction with the corresponding visual indicator, the selected operating mode prior to the processor determining the temperature of the living being;

wherein the control unit comprises:

a transmitter configured to send a control signal from the control unit;

a receiver configured to receive a status signal sent to the control unit; and a user interface operable to produce a switch signal, the switch signal included in the control signal;

wherein the switch of the thermometer is operable by use of the switch signal from the control unit.

42. The system of claim 41, wherein communication between the control unit and the thermometer comprises wireless communication.

43. The system of claim 41, wherein the control unit comprises:

a cradle configured to accept the thermometer; and a communication interface configured to communicate with a cooperating connector on the thermometer when the thermometer is positioned on the cradle.

44. The system of claim 41, wherein the plurality of first indicators comprises a single light source capable of illuminating with a plurality of colors, wherein each color corresponds to one of the first indicators.

45. The system of claim 41, wherein the plurality of first indicators comprises a single light source capable of illuminating with a plurality of intensity levels, wherein each intensity level corresponds to one of the first indicators.

46. The system of claim 41, wherein each of the visual indicators comprises text or graphics.

47. The system of claim 41, wherein the completion indicator comprises at least one lighting element.

48. The system of claim 41, wherein the completion indicator, when activated, backlights the display.

49. The system of claim 41, wherein the completion indicator comprises audible feedback.

50. The system of claim 41, wherein each of the first indicators comprises a light source.

51. The system of claim 50, wherein the light source is an LED.

52. The system of claim 41, wherein the first indicators are provided as part of an output display.

53. The system of claim 52, wherein the output display is an LCD.

54. The system of claim 41, wherein the visual indicators are provided as part of an output display.

55. The system of claim 54, wherein the output display is an LCD.

56. The system of claim 41 further comprising an output display including a light source capable of illuminating with a plurality of colors, wherein each operating mode includes a plurality of temperature ranges, with each temperature range corresponding to a temperature condition of the living being, and each of the plurality of colors corresponding to one of the temperature ranges.

57. The system of claim 56, wherein the light source is an LED.

58. The system of claim 56, wherein the light source is a backlight light source.

* * * * *